United States Patent [19]

Bock et al.

[11] Patent Number: 5,204,349

[45] Date of Patent: Apr. 20, 1993

[54] AMIDE-SUBSTITUTED DERIVATIVES OF SPIROINDANYLCAMPHORSULFONYL OXYTOCIN ANTAGONISTS

[75] Inventors: Mark G. Bock, Hatfield; Ben E. Evans; Roger M. Freidinger, both of Lansdale; Kevin Gilbert, Bechtelsville; Doug W. Hobbs, Lansdale; James B. Hoffman, King of Prussia; George F. Lundell, Blue Bell; Douglas J. Pettibone, Chalfont, all of Pa.

[73] Assignee: Merck & Co., Inc., Rahway, N.J.

[21] Appl. No.: 760,284

[22] Filed: Sep. 16, 1991

[51] Int. Cl.[5] .................. A61K 31/495; C07D 471/00; C07D 401/12
[52] U.S. Cl. .................... 514/253; 514/278; 544/230; 546/17
[58] Field of Search .................. 544/230; 546/17; 514/253, 278

[56] References Cited

U.S. PATENT DOCUMENTS 3,301,857  1/1967  Berger et al. ............... 260/288
3,654,287  4/1972  Dykstra et al. ............. 260/293.62
3,666,764  5/1972  Campbell et al. ........... 260/293.62
4,379,933  4/1983  Ong et al. ..................... 546/17

OTHER PUBLICATIONS

J. Parm. Sci (1982) 71, 3 pp. 291–294, by Crooks, et al.
J. Org. Chem. (1971) 36, 5, pp. 650–654, by Matier, et al.
J. Org. Chem. (1976) 41, 15, pp. 2528–2633, by Parkam, et al.
J. Chromatography (1977) 136, pp. 401–407, by Bryce, et al.

Primary Examiner—C. Warren Ivy
Assistant Examiner—Ba K. Trinh
Attorney, Agent, or Firm—Frank P. Grassler; Charles M. Caruso

[57] ABSTRACT

Compounds of the formula:

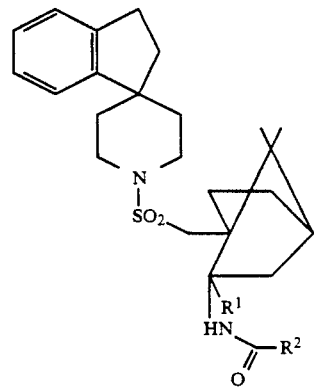

where $R^1$ is hydrogen or hydroxy and $R^2$ is a substituted amino group, a substituted heterocyclic ring or a substituted alkyl. These compounds are oxytocin and vasopressin antagonists useful in the treatment of preterm labor, dysmenorrhea and for the stoppage of labor preparatory to cesarean delivery, timing of parturition, uterine hyperactivity, endometriosis, hypertension, congestive heart failure, hyponatremia and cognitive disorders. Also disclosed are pharmaceutical compositions containing these compounds, methods of their use and methods of their preparation.

6 Claims, No Drawings

AMIDE-SUBSTITUTED DERIVATIVES OF SPIROINDANYLCAMPHORSULFONYL OXYTOCIN ANTAGONISTS

FIELD OF THE INVENTION

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such a oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of formula I are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparation to Cesarean delivery.

The compounds of the present invention are those of the general structural formula:

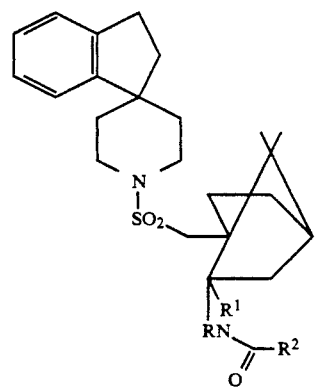

and the pharmaceutically acceptable salts thereof, wherein

R is H or alkylsulfonylalkyl,

R¹ is hydrogen or hydroxy,

R² is one of N-(R³)₂, Het-R⁴ or Alk-R⁵, wherein

R³ is independently one or more of hydrogen, cycloalkyl, pyrrolidinyl substituted by oxo, carboxyalkyl or alkoxycarbonylalkyl, alkyl substituted by alkylamino, alkylcarbamate, alkylcarbonyl, alkylsulfonyl, alkylthio, alkoxycarbonyl, amino, aminocarbonyl, carboxyl, dialkylamino, dialkylaminoaryl, hydroxyl, sulfhydryl, or substituted or unsubstituted 5 or 6 membered heterocyclic rings having 1 or 2 heteroatoms where said heteroatom is N and said ring substitutent is aralkoxycarbonyl;

Het is a 5 or 6 membered heterocyclic ring having 1 heteroatom wherein said heteroatom is N, $R^4$ is alkylsulfonyl, alkylsulfonylamino, alkylsulfonyloxy, alkylaminocarbonyl, alkylcarbamatealkylcarbonyl, alkoxycarbonyl, alkoxycarbonylalkyl, aminocarbonylalkyl, aminoalkylcarbonyl, aralkoxycarbonyl, carbonyl, dialkylaminocarbonyl, dialkylaminoalkylcarbonyl, diaminoalkylcarbonyl, halogenalkyl, halogenalkylcarbonyl, halogenalkoxycarbonyl, hydroxy, hydroxyalkyl, hydroxyalkylcarbonyl, imidazolylalkylcarbonyl imidizinylalkylcarbonyl, or phthalimidinylalkyl; with the proviso for Het-R4 that Het cannot be mono-substituted by any one of the alkoxycarbonyl, alkoxycarbonylalkyl, aralkoxycarbonyl or hydroxy;

Alk is alkyl, $R^5$ is independently one or more of $R^6$, or Het-$R^7$ wherein $R^6$ is independently one or more of alkylcarbamate, alkylcarbonylamino substituted by substituted imidazolyl or pyrrolidinyl rings where said ring substituent is alkyl or alkoxycarbonylalky, alkylcarbamatecycloalkyl, alkylcarbonylaminoalkylsulfonyl, alkylimidazolylthio, alkylimidizinylthio, alkylimidazolylalkylthio, alkylimidizinylalkylthio, alkylpyrrolidinylthio, alkylpyrrolidinylalkylthio, alkylsulfonyl, alkylsulfonylamino, alkylsulfonylalkylamino, alkoxycarbonyl, alkoxycarbonylalkylamine, alkoxycarbonylalkylcarbonylamine, alkoxycarbonylalkylsulfonylamine, amino, aminocarbonyl, aminoalkylcarbonylamino, aminocarbonylalkylsulfonyl, aminocarbonylalkylearbonylamino, aralkoxy, aralkoxycarbonyl, aralkylcarbamate, arylcarbamate, arylcarbamatecarbonylamino, arylcarbamatealkylcarbonylamino, carboxyalkylamino, carboxyalkylcarbonylamino, carboxyalkylsulfonylamino, cyano, cyanoalkylcarbonylamino, dialkylaminoalkylcarbonylamino or oxo, with the proviso for $R^6$ that $R^6$ cannot be mono-substituted by any one of alkoxycarbonyl, alkylcarbamate, alkylsulfonyl, aralkylcarbamate, aralkoxy, amino, aminocarbonyl, or oxo;

Het is as defined before;

$R^7$ is one or more of alkyl, imidazolinylalkylcarbonyl, imidazolinylalkylcarbonylamino, oxo, pyrrolidinylalkylcarbonyl, pyrrolidinylalkylcarbonylamino or alkylamino substituted by one or more of alkylcarbamate, alkylcarbamatealkylcarbonyl, alkylsulfonylalkyl, amino, aralkoxyalkyl or oxo with the proviso for Het-$R^7$ that Het cannot be mono-substituted by alkyl alkylamino, dialkylamino or oxo.

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | Oxalate |
| Dihydrochloride | Pamoate (Embonate) |
| Edetate | Palmitate |
| Edisylate | Pantothenate |
| Estolate | Phosphate/diphosphate |
| Esylate | Polygalacturonate |
| Fumarate | Salicylate |
| Gluceptate | Stearate |
| Gluconate | Subacetate |
| Glutamate | Succinate |
| Glycollylarsanilate | Tannate |
| Hexylresorcinate | Tartrate |
| Hydrabamine | Teoclate |
| Hydrobromide | Tosylate |
| Hydrocloride | Triethiodide |
| Hydroxynaphthoate | Valerate |
| Iodide | |
| Isethionate | |
| Lactate | |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes, alkenes and alkynes with one or more degrees of unsaturation at any position on the chain, of one to ten total carbon atoms or any number within this range.

The term "aryl" shall mean phenyl.

The term "cycloalkyl" shall mean cyclic rings of alkanes, alkenes or alkynes with one or more degrees of unsaturation at any position of the ring, of three to eight total carbon atoms.

Whenever the terms "alkyl" or "aryl" or either of their prefix roots appear in a name of a substituent (e.g. aralkoxyaryloxy) they shall be interpreted as including those limitations given above for "alkyl" and "aryl". Designated numbers of carbon atoms (e.g. $C_{1-10}$) shall refer independently to the numberof carbon atoms in an alkyl or cyclic alkyl moiety or to the alkyl portion of a larger substituent in which alkyl appears as its prefix root.

The term "oxo" shall refer to the substituent=O.

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "substituted" shall be deemed to include multiple degrees of substitution by a named substitutent.

The ability of the compounds of formula I to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

Because of the known relationship of vasopressin to oxytocin, the compounds of the present invention are also useful as vasopressin antagonists. Vasopressin antagonists are useful in the treatment or prevention of disease states involving vasopressin disorders, including their use as diuretics and their use in congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polyactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of formula I can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

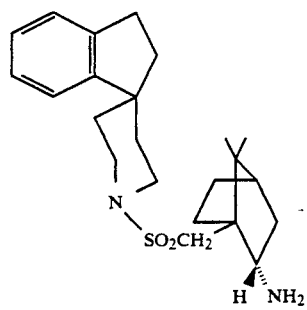
↓ ClCO₂CH₂CH₃
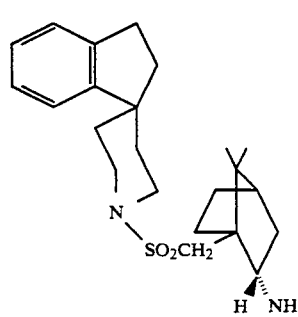
EXAMPLE 4
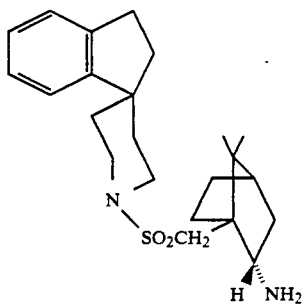
↓
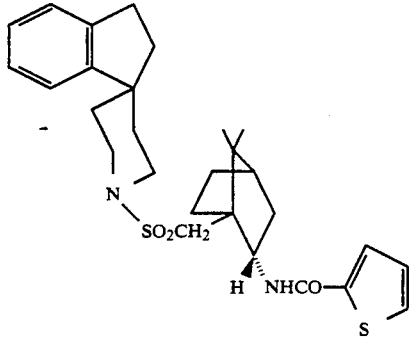
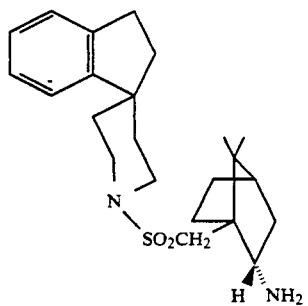
↓ ClCOCH₂CH=CH₂
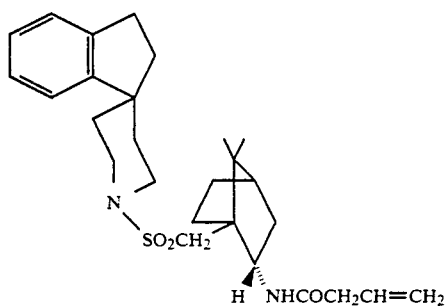
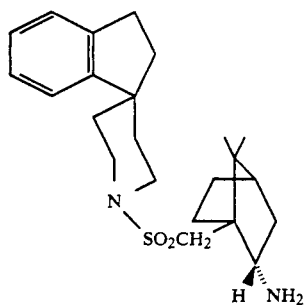
↓ ClSO₂N(CH₃)₃
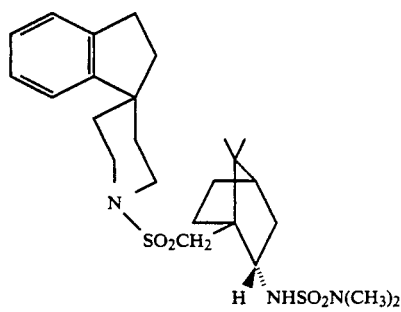

EXAMPLE 5
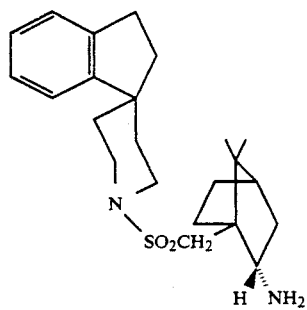
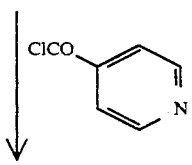
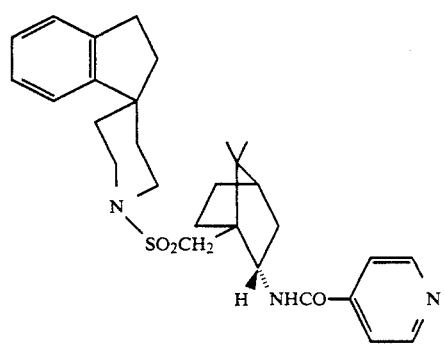
EXAMPLE 6
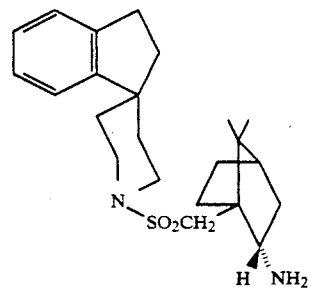
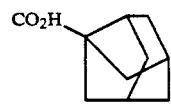
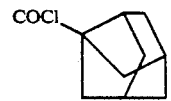
EXAMPLE 6
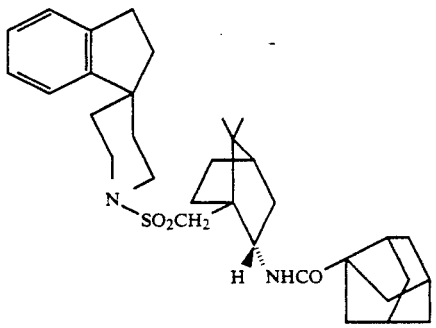
EXAMPLE 8
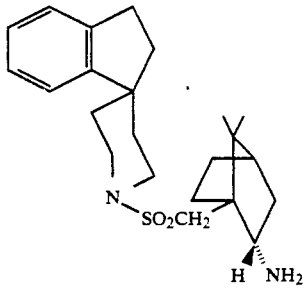
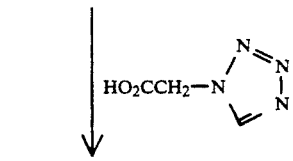
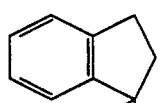
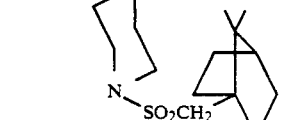
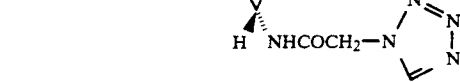

REACTION SCHEMES, PART 2
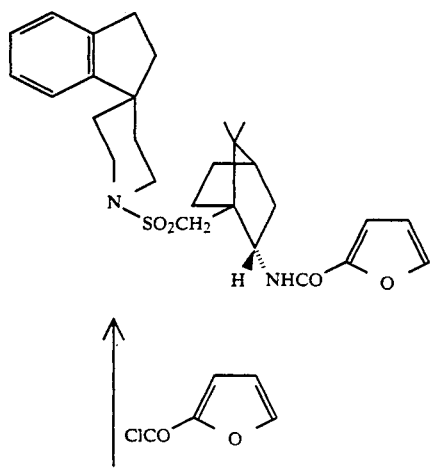
↑ ClCO⟨furan⟩
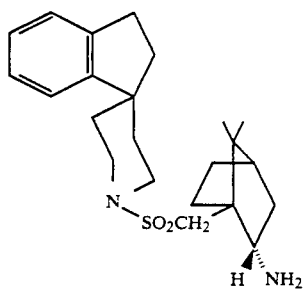
↓ 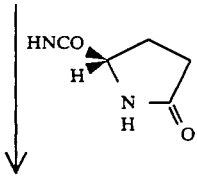
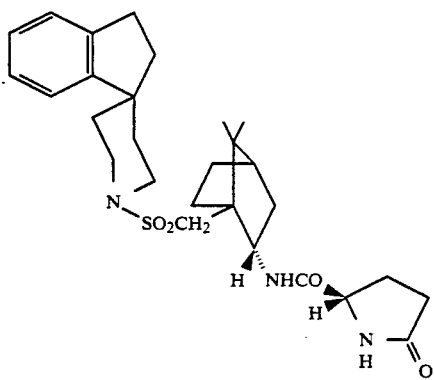
REACTION SCHEMES, PART 3
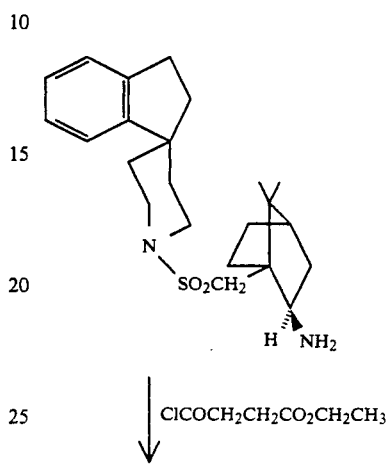
↓ ClCOCH2CH2CO2CH2CH3
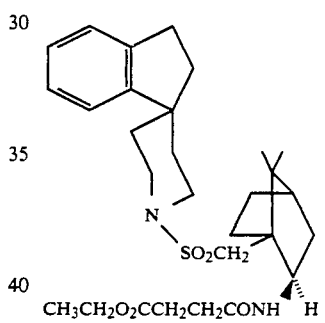
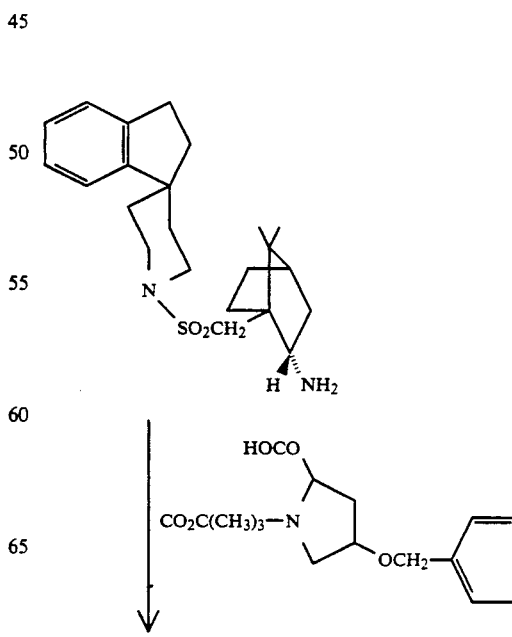

-continued
REACTION SCHEMES, PART 3
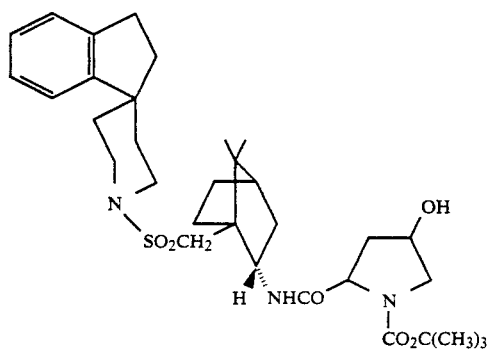
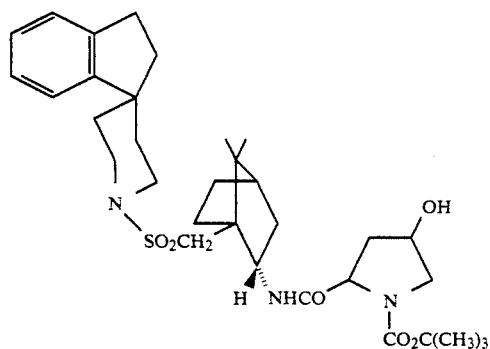
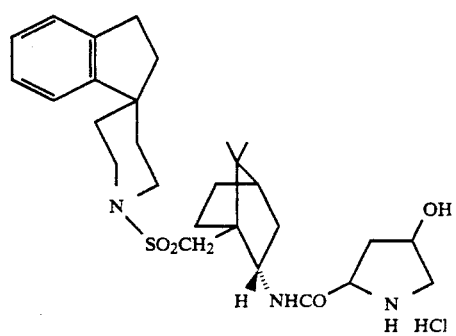
-continued
REACTION SCHEMES, PART 3
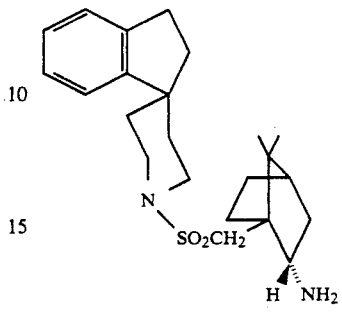
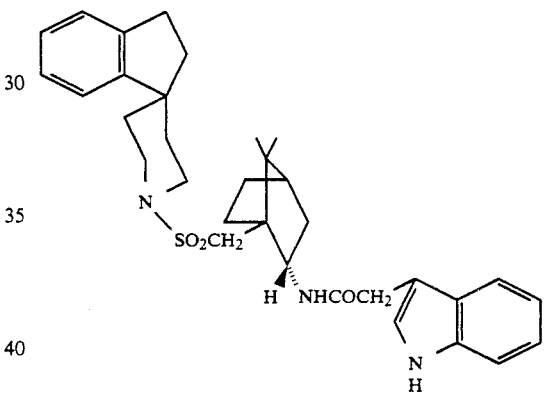
REACTION SCHEMES, PART 4
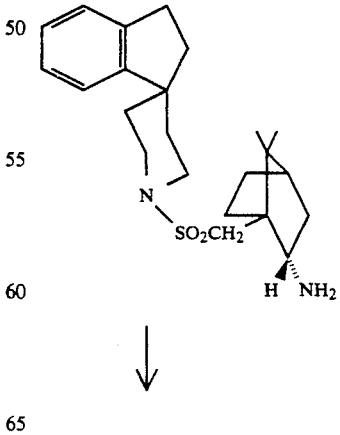

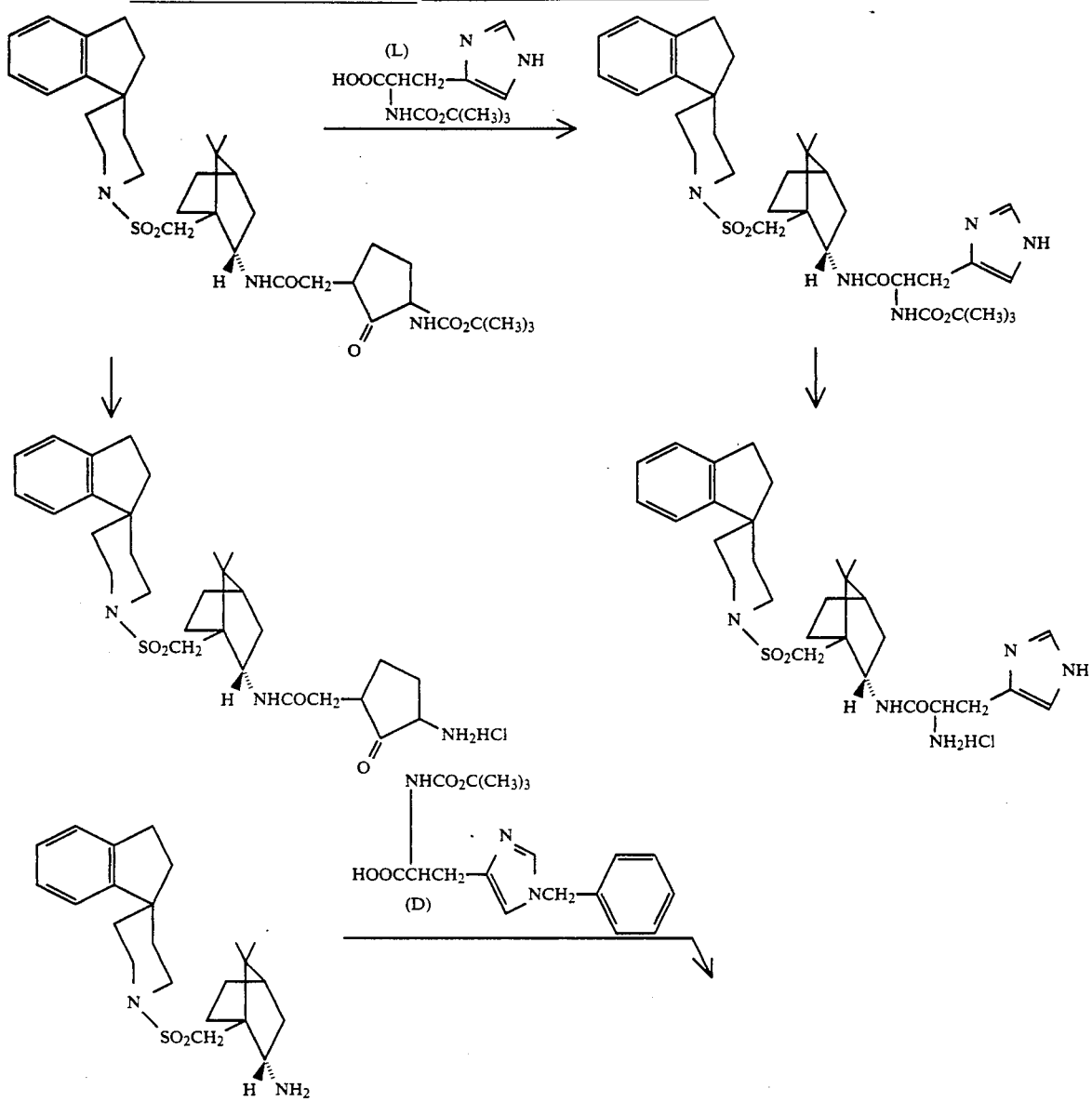

-continued
REACTION SCHEMES, PART 5
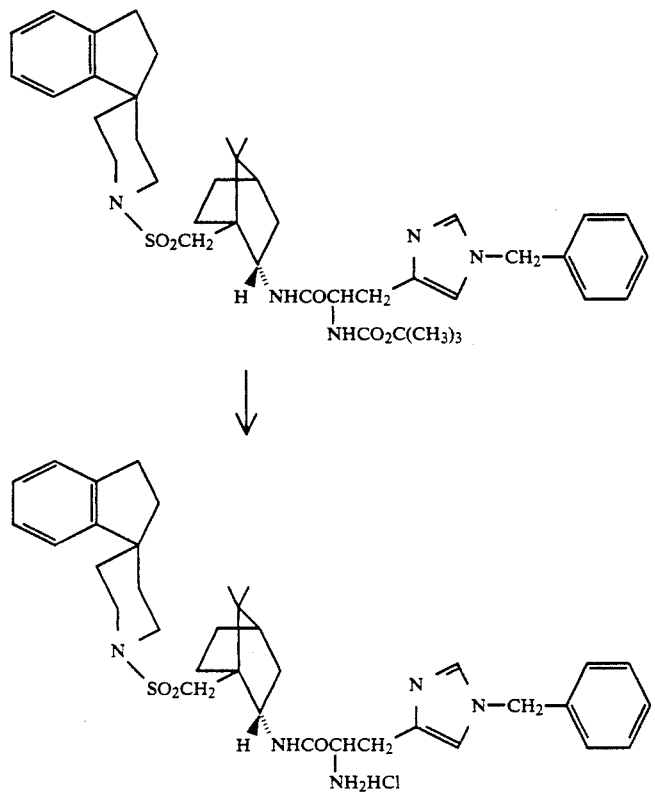
40
REACTION SCHEMES, PART 6
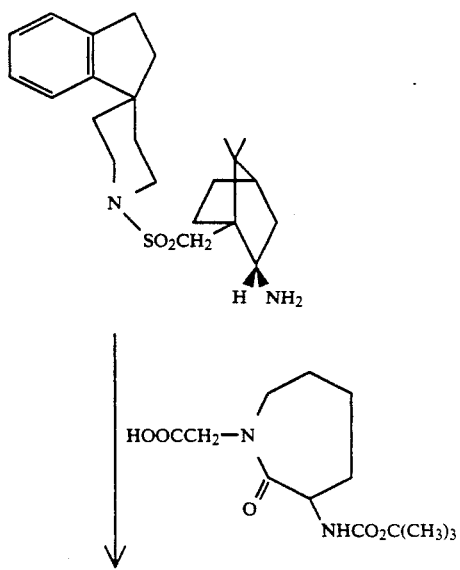
-continued
REACTION SCHEMES, PART 6
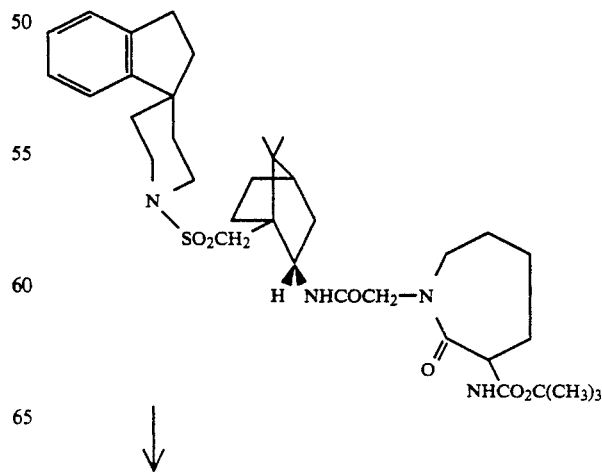

5,204,349
-continued
REACTION SCHEMES, PART 6
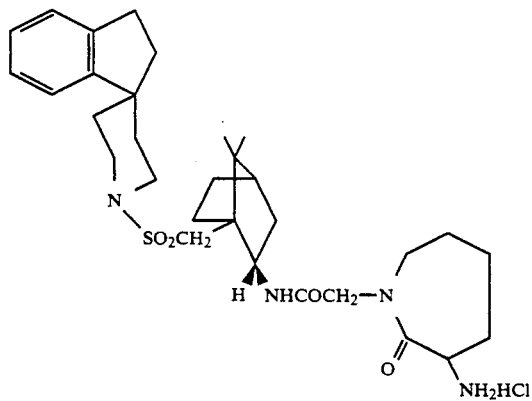
REACTION SCHEMES, PART 7
(ClCH₂CH₂)₂NH HCl + [(CH₃)₃COCO]₂O
↓ Et₃N
(ClCH₂CH₂)₂NCO₂-t-Bu
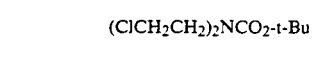 + (ClCH₂CH₂)₂NCO₂-t-Bu
↓ LiN[Si(CH₃)₃]₂
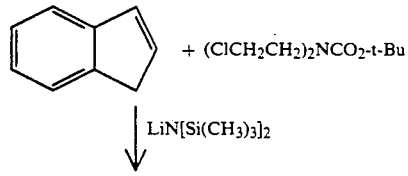
↓ HCl, EtOAc
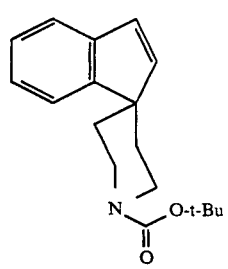 + 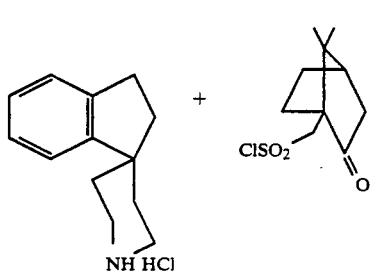
↓ Et₃N
-continued
REACTION SCHEMES, PART 7
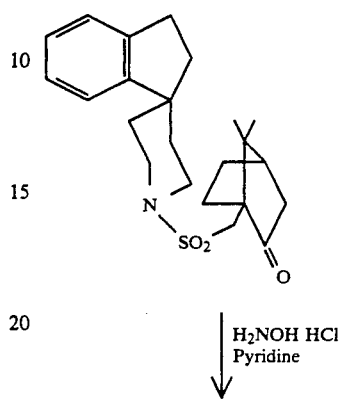
↓ H₂NOH HCl
   Pyridine
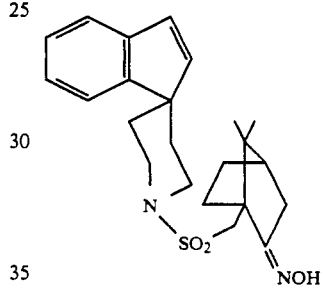
↓ Ni(R), H₂
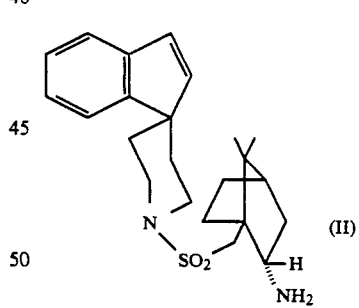    (II)
+
Endo Isomer
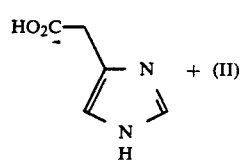 + (II)
1. EDC, HBT, NEt₃, DMF
2. HCl
↓

-continued
REACTION SCHEMES, PART 7

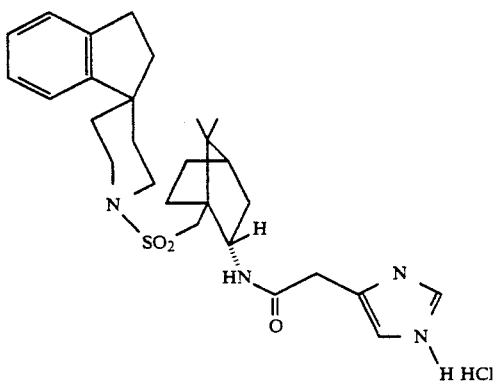

EXAMPLE A

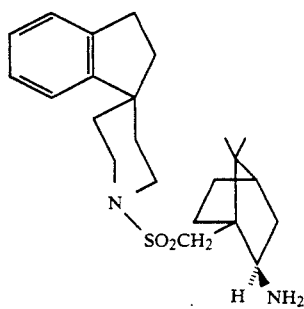

Endo-(1S)-1'-(((2-amino-7,7-dimethylbicyclo(2.2.1)-hept-1-yl)-methyl)-sulfonyl)spiro(1H-indan-1,4'-piperidine)

Di-t-butyl dicarbonate (31 g, 0.14 mole available from Aldrich) and bis(2-chloroethyl) amine hydrochloride (21.6 g, 0.12 mole Aldrich) were combined in $CH_2Cl_2$ (250 ml) stirred at ambient temperature and treated with triethylamine (12.8 g, 0.127 mole) added dropwise over 15 minutes. After 1 hour, another 1.5 ml of triethylamine was added. After a total of 2.5 hours, the mixture was poured onto a silica gel column packed with $CH_2Cl_2$:hexane (1:1), and eluted with $CH_2Cl_2$. The combined product fractions were evaporated to dryness in vacuo to give N,N-bis(2-chloroethyl)-t-butyl-carbamate.

To a solution of indene (10.3 g, 89 mmole) in dry tetrahydrofuran (THF, 18 ml) cooled in an ice bath and maintained under a nitrogen blanket was added lithium bis(trimethylsilyl)amide (Aldrich, 177 ml of a 1.0M solution in THF; 177 mmole) over 15 minutes. The mixture was stirred in the cold for 30 minutes, then added over 15 minutes to a solution of N,N-bis(2-chloroethyl)-t-butylcarbamate (21.2 g, 88 mmole) stirred in an ice bath. The mixture was stirred for 2 hours in the cold and for 30 minutes at ambient temperature under nitrogen, then evaporated in vacuo to a foam. $CH_2Cl_2$ was added and the resulting mixture poured onto a silica gel column packed with 40% hexane in $CH_2Cl_2$. The column was eluted with 40% hexane in $CH_2Cl_2$ followed by $CH_2Cl_2$, and the product fractions were evaporated to dryness in vacuo to provide 1'-(t-butyloxycarbonyl)-spiro(indene-1,4'-piperidine).

1'-(t-Butyloxycarbonyl)spiro(indene-1,4'-piperidine) (16 g, 56 mmole) in ethyl acetate (250 ml) was stirred in an ice bath and saturated with HCl(g) for 30 minutes. The mixture was evaporated to dryness. Ethyl acetate was added and removed in vacuo three times, and the residue was triturated with diethyl ether and filtered to provide spiro(1H-indene-1,4'-piperidine) hydrochloride. The free base was obtained by slurrying the hydrochloride in aqueous sodium bicarbonate solution and extracting with $CH_2Cl_2$. The organic layer was separated, dried over sodium sulfate, filtered, and evaporated to dryness in vacuo to provide spiro(1H-indene-1,4'piperidine).

Spiro(1H-indene-1,4'piperidine) (308 mg, 1.66 mmol) and (+)-10-camphorsulfonyl chloride (418 mg, 1.66 mmol) were combined in $CH_2Cl_2$ and treated with triethylamine (0.23 ml). The mixture was stirred at ambient temperature for 15 minutes, then poured onto a silica gel column and eluted with 1:1 $CH_2Cl_2$:hexane. The product fractions were combined and evaporated to dryness in vacuo to provide (1S)-1'-(((7,7-dimethyl-2-oxobicylo(2.2.1) hept-1-yl)-methyl)sulfonyl)spiro(1H-indene-1,4'-piperidine) as a solid which was recrystallized from petroleum ether and dried overnight in vacuo at ambient temperature.

(1S)-1'-(((7,7-dimethyl-2-oxobicyclo(2.2.1) hept-1-yl)methyl)sulfonyl)spiro(1H-indene-1,4'-piperidine) (30 g, 0.075 mole) in pyridine (500 mL) was heated in an oil bath to 70° C. (internal). Hydroxylamine hydrochloride (30 g) was added in three portions over ca. 20 minutes. After 2 hours, an additional 10 g of hydroxylamine hydrochloride was added (over 10 minutes). At 30, 40, and 50 minutes additional elapsed time, further 3 g lots of hydroxylamine hydrochloride were added. After another 30 minutes, the mixture was poured into water (2 L) and extracted 3 times with ethyl acetate (300 mL portions). The organic layers were combined, washed with 1N HCl (600 mL total), dried over sodium sulfate, filtered, and evaporated to dryness in vacuo. EtOH (abs; ca. 250 mL) was added to the resulting thick syrup and the solution allowed to stand at ambient temperature overnight. The mixture was filtered and the filtrate boiled down to ca. 80 mL. After standing, the mixture was again filtered and boiled down to ca. 20 mL. After a third filtration, the filtered solids were combined to give (1S)-1'-(((7, 7-dimethyl-2-oximinobicyclo(2.2.1-)hept-1yl)-methyl) sulfonyl)spiro(1H-indene-1,4'-piperidine) (28 g).

Freshly prepared, activated Raney Nickel catalyst (ca. 30 g) in water was allowed to settle and the water decanted. Abs. ethanol (300 mL) was added, and the mixture swirled and again allowed to settle. The solvent was decanted. Two more washdecant cycles with 150 mL of ethanol were similarly carried out. (1S)-1'-(((7,7-dimethyl-2-oximinobicyclo (2.2.1)hept-1-yl)methyl)sulfonyl)-spiro(1H-indene-1, 4'-piperidine) (30 g) was stirred in a mixture of abs. ethanol (450 mL) and 2-methoxyethanol (900 mL), nitrogen was bubbled through the suspension/solution, and the Raney Nickel catalyst was added. The mixture was hydrogenated under 50 psi overnight. TLC (9:1 $CH_2Cl_2$MeOH, silica gel) showed the reaction to be complete. The catalyst was removed by filtration, and the filtrate evaporated to dryness in vacuo. The crude solid (27 g) was divided into 7 g batches, and each batch was dissolved in methylene chloride (ca. 200 mL) and flash chromatographed on silica (700 g in a 100 mm column, packed and eluted with 8% (v/v) methanol in methylene chloride), taking 200 mL fractions. The exo isomer of the title amine was obtained in fractions ca. 5-7, and the desired endo isomer in fractions ca. 8-16. TLC was on silica, eluted with 8% methanol-methylene chloride, phosphomolybdic acid stain. The combined product fractions were evaporated to dryness to provide the title compound (4.5 g from each 7 g lot, ca. 18 g total) as a colorless solid.

Abbreviations used in the Examples are as follows:

| TEA | = triethylamine |
|---|---|
| DIEA | = diisopropylethylamino |
| BOP | = benzotriazol-yloxytris(dimethylamino) phosphonium hexafluorophosphate |
| THF | = tetrahydrofuran |
| DMF | = dimethylformamide |
| LAH | = lithium aluminum hydride |
| TFA | = trifluoroacetic acid |
| HPLC | = 15 min. linear gradient |
| Method A | 95:5 A:B to 0:100 A:B |
| | A - H₂O containing 0.1% by vol. TFA |
| | B = CH₃CN containing 0.1% by vol. TFA |
| | 2.0 mL/min flow rate |
| | 12 cm C₁₈ reverse phase column |
| | UV detection (215 nm) |

TLC was performed on 20 cm plates coated with silica gel (250 microns) from Analtech.

EXAMPLE 1

(1S)-1'-(((7,7-dimethyl-2-endo-(4-nitrophenyloxycarbonylamino)-bicyclo-(2,1,1)-kept-1-yl)-methyl)sulfonyl)spiro(1H-indene-1,4'-piperdine)

The product of Example A [3.47 mmol] and 4-nitrophenyl chlorofomate [3.64 mmol] were combined in THF. The reaction mixture was treated with triethylamine [4.54 mmol] and allowed to stir for 2 hours. The reaction mixture was concentrated to dryness and the resulting residue was purified by a silica gel column, while eluting with 1% ethyl acetate in methylene chloride. The product fractions were combined and concentrated to dryness in vacuo. The title compound was obtained as a white solid from ether.

EXAMPLE 2

The product of Example 1 [0.278 mmol] and (benzyloxycarbonyl)piperazic acid [0.334 mmol] were combined in DMF. The reaction mixture was treated with triethylamine [0.401 mmol] and allowed to stir for 2 hours. The reaction mixture was concentrated to dryness and the resulting residue was dissolved in $CH_2Cl_2$. This solution was placed on a silica gel column and eluted with 5% methanol in $CH_2Cl_2$ and then with 96/4/0.4 of $CH_2Cl_2$/methanol/acetic acid. The product fractions were combined and evaporated to dryness. The title compound was obtained as a white solid from ether and was dried in vacuo overnight.

m.p.: 90°-120° C.
NMR: Consistent with structure.
HPLC: >98% pure.
FAB MS: M+H+ −693.6.
CHN: Calc'd for $C_{37}H_{48}N_4O_7S.0.20\ C_4H_{10}O.0.25\ H_2O$: Calc'd: C, 63.74; H, 7.15; N, 7.87. Found: C, 63.78; H, 7.08; N, 7.81.

EXAMPLE 3

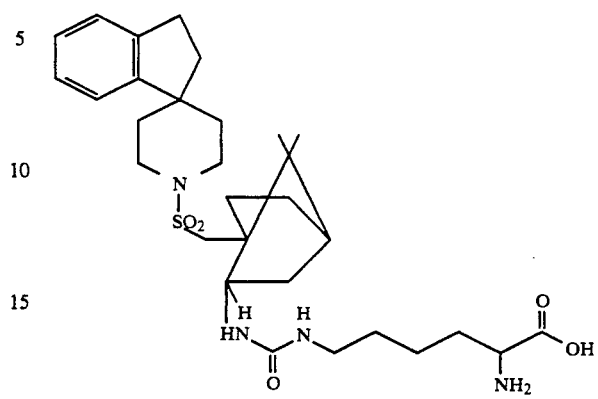

The procedure of Example 2 was carried out using the product of Example 1 [0.196 mmol] triethylamine [0.438 mmol], and substituting N-α-(t-butoxycarbonyl)-L-lysine [0.217 mmol] for (benzyloxycarbonyl)piperazic acid. Chromatographic elution was with 5% methanol in $CH_2Cl_2$ and then 96/4/0.4 of $CH_2Cl_2$/methanol-/acetic acid. A white solid was obtained from ether. This white solid was dissolved in ethyl acetate, cooled to 0° C. and treated with a saturated solution of HCl in ethyl acetate. The reaction mixture was stirred for 30 minutes and then concentrated to dryness. The title compound was obtained as a white solid from ether and was dried in vacuo overnight.

m.p.: 80°-205° C.
NMR: Consistent with structure.
HPLC: >98% pure.
FAB MS: M+H=575.3 (free base).
Elem. Anal Calc'd for $C_{30}H_{46}N_4O_5S.HCl.0.30$ mmol $C_4H_8O_2.0.90\ H_2O$; Calc'd: C, 57.30; H, 7.89, N, 8.57. Found: C, 57.30; H, 7.61, N, 8.55.

EXAMPLE 4

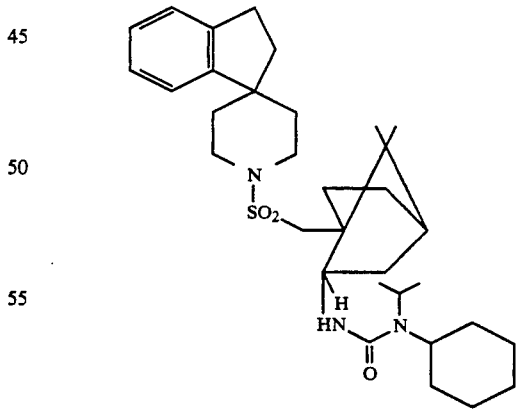

The procedure of Example 2 was carried out using the product of Example 1 [0.174 mmol], triethylamine [0.250 mmol], and substituting N-isopropylcyclohexylamine [0.209 mmol] for (benzyloxycarbonyl)piperazic acid. Chromatographic elution was with 5% ether in $CH_2Cl_2$. The title compound was obtained as a white solid from ether and dried in vacuo, overnight.

m.p.: 71°-85° C.

NMR: Consistent with structure.
HPLC: >96% pure.
FAB MS: M+H+ =570.4.
Elem. Anal Calc'd for $C_{33}H_{51}N_3O_3S$: Calc'd: C, 69.55; H, 9.02, N, 7.37. Found: C, 69.53; H, 9.08, N, 7.29.

EXAMPLE 5

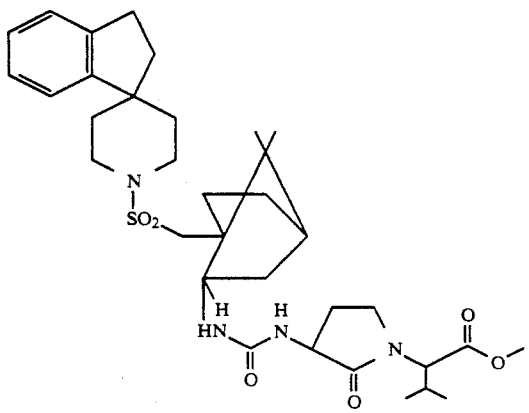

The procedure of Example 2 was carried out using the product of Example 1 [00.244 mmol], triethylamine [0.52 mmol] and substituting 3-amino-1-(1-methoxycycarbonyl-2-methylpropyl)-pyrrolidin-2-one [0.26 mmol] for (benzyloxycarbonyl) piperazic acid. Chromatographic elution was with 5% ether in $CH_2Cl_2$, 1% methanol in $CH_2Cl_2$ and 2% methanol in $CH_2Cl_2$. The title compound was obtained as a white solid from ether and dried in vacuo, overnight.

m.p.: 85°–121° C.
NMR: Consistent with structure.
HPLC: >91% pure.
FAB MS: M+H+ =643.4.
Elem. Anal Calc'd for $C_{34}H_{50}N_4O_6S.0.45$ $H_2O$: Calc'd: C, 62.73; H, 7.88, N, 8.61. Found: C, 62.68; H, 7.70, N, 8.99.

EXAMPLE 6

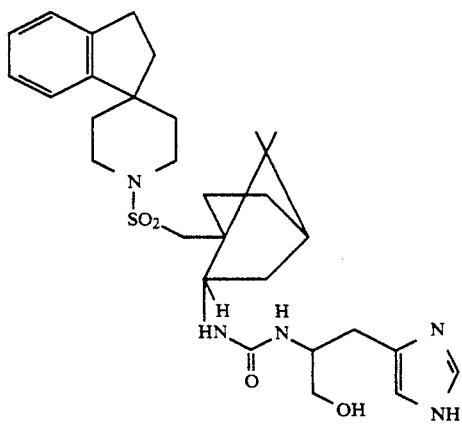

The procedure of Example 2 was carried out using the product of Example 1 [0.172 mmol] triethylamine [0.453 mmol], and substituting L-histidinol dihydrochloride [0.206 mmol] for (benzyloxycarbonyl) piperazic acid. Chromatographic elution was with 5% methanol in $CH_2Cl_2$ and then with 95/5/0.5 of $CH_2Cl_2$/methanol/ammonium hydroxide. The title compound was obtained as a white solid from ether and dried in vacuo, overnight.

m.p.: 90°–193° C.
NMR: Consistent with structure.
HPLC: >98% pure.
FAB MS: M+H+ =570.4.
Elem. Anal Calc'd for $C_{30}H_{43}N_5O_4S.0.25$ $C_4H_{10}O.0.30$ $H_2O$: Calc'd: C, 62.71; H, 7.83, N, 11.80. Found: C, 62.73; H, 7.79, N, 11.75.

EXAMPLE 7

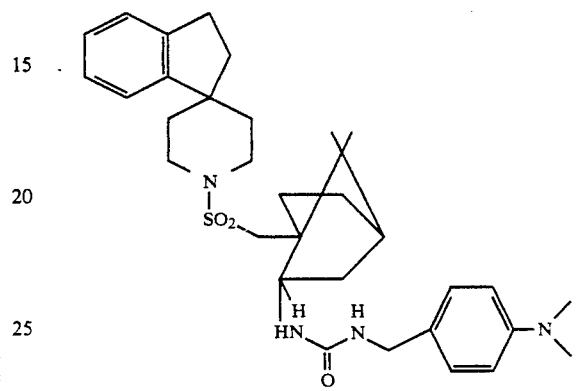

The procedure of Example 2 was carried out using the product of Example 1 [0.180 mmol], triethylamine [0.458 mmol], and substituting 4-(dimethylamino)benzylamine dihydrochloride [0.208 mmol] for (benxyloxycarbonyl)piperazic acid. Chromatographic elution was with 5% ether in $CH_2Cl_2$ and then with 3% methanol in $CH_2Cl_2$. The title compound was obtained as a white solid from ether and dried in vacuo, overnight.

m.p.: 82°–110° C.
NMR: Consistent with structure.
HPLC: >95% pure.
FAB MS: M+H+ =579.4.
Elem. Anal. Calc'd for $C_{33}H_{46}N_4O_3S$: Calc'd: C, 68.48; H, 8.01, N, 9.68. Found: C, 68.25; H, 8.00, N, 9.68.

EXAMPLE 8

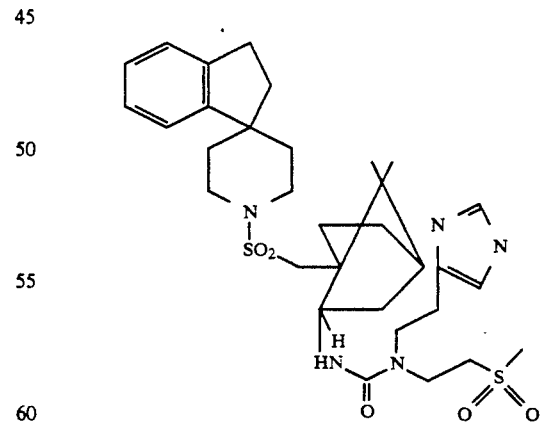

Step 1

Histamine [13.3 mmol] and methyl vinyl sulfone [4.6 mmol] were combined in methanol and allowed to stir for 4 hours. The reaction mixture was concentrated to dryness and the resulting residue was dissolved in $CH_2Cl_2$. The $CH_2Cl_2$ solution was poured onto a silica gel column and eluted with 93/7/0.7 of CH$_2$Cl$_2$/methanol/ammonium hydroxide. The product fractions were combined and evaporated to dryness in vacuo to yield 4-(2-(N-(2-methanesulfonylethyl)amino)ethyl-)imidizole.

Step 2

The procedure of Example 2 was carried out using the product of Example 1 [0.188 mmol], triethylamine [0.228 mmol], and substituting 4-(2-(N-(2-(methansulfonylethyl)amino)ethyl)imidizole [0.368 mmol] for (benzyloxycarbonyl)piperazic acid. Chromatographic elution was with 3% methanol in CH$_2$Cl$_2$ and then with 95/5/0.5 of CH$_2$Cl$_2$/methanol/ammonium hydroxide. The title compound was obtained as a white solid from ether and dried in vacuo, overnight.

m.p.: 76°–161° C.
NMR: Consistent with structure.
HPLC: >99% pure.
FAB MS: M+H+ =646.2.
Elem. Anal Calc'd for C$_{32}$H$_{47}$N$_5$O$_5$S$_2$.0.15 C$_4$H$_{10}$O.0.15 CH$_2$Cl$_2$.0.45 H$_2$O: Calc'd: C, 58.03; H, 7.39, N, 10.33. Found: C, 57.98; H, 7.32, N, 10.49.

EXAMPLE 9

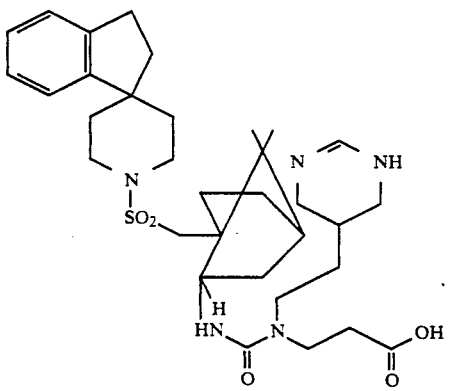

Step 1

Histamine [13 mmol] and ethylacrylate [4.61 mmol] were combined in methanol and allowed to sire 12 hours. The reaction mixture was concentrated to dryness and the resulting residue was dissolved in CH$_2$Cl$_2$. The CH$_2$Cl$_2$ solution was poured onto a silica gel column and eluted with 93/7 0.7 of CH$_2$Cl$_2$/methanol/ammonium hydroxide. The product fractors were combined and evaporated to dryness in vacuo to yield 4-(2-(N-(2-ethocycarbonylethyl)amino)ethyl)imidizole.

Step 2

The procedure for L-368,646 was carried out using (1S)-1'-(((7,7-dimethyl-(2-endo-(4-nitrophenyloxycarbonylamino)-bicyclo-(2,2,1)-hept-1-yl)-methyl)sulfonyl)spiro(1H-indene-1,4'-piperdine) [0.69 mmol], triethylamine [1.56 mmol], and substituting 4-(2-(N-(2-ethoxycarbonylethyl)amino)ethyl)imidizole [1.42 mmol] for (benzloxycarbonyl) piperazic acid. Chromatographic elution was with 5% methanol in CH$_2$Cl$_2$ and then with 95/5/0.5 of CH$_2$Cl$_2$/methanol/ammonium hydroxide. A white solid was obtained form ether and dried in vacuo, overnight. This white solid was combined with 1.95M sodium hydroxide in methanol. The reaction mixture was allowed to stir for 72 hours and then concentrated to dryness. The resulting residue was partitioned between ethyl acetate and water. The ethyl acetate layer was dried over sodium sulfate, filtered, and the filtrate was concentrated to dryness. The residue was purified by a silica gel column, eluted with 91/10/1/1 of CH$_2$Cl$_2$/methanol/water/acetic acid. The product fractions were combined and concentrated to dryness. The title compound was obtained as a white solid from ether, and dried in vacuo, overnight.

m.p.: 63°–132° C.
NMR: Consistent with structure.
HPLC: >99% pure
FAB MS: M+H+ =612.2.
Elem. Anal Calc'd for C$_{32}$H$_{45}$N$_5$O$_5$S.0.20 C$_4$H$_{10}$O.0.80 C$_2$H$_4$O$_2$.1.35 H$_2$O: Calc'd: C, 59.10; H, 7.63, N, 10.02. Found: C, 59.11; H, 7.24, N, 10.07.

EXAMPLE 10

Endo-(1S)-1'-(((2-(L-2(4-imidazole acetylamino) glutaramyl)amino-7,7-dimethylbicyclo(2,2,1)hept-1-yl)-methyl)-sulfonyl)spiro-(1H)-indan-1.4'-piperidine

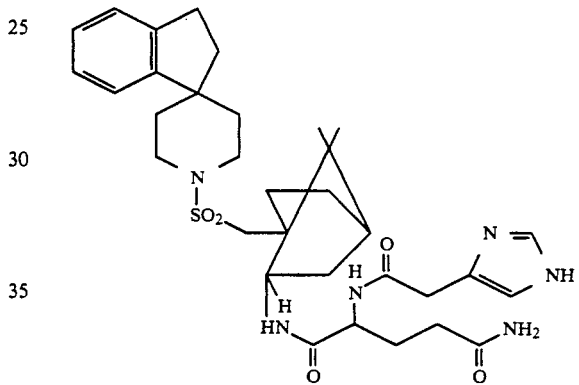

Step 1:

Endo-(1S)-1'-(((2-(L-2(tertbutoxycarbonylamino) glutaramyl)amino-7,7-dimethylbicyclo(2,2,1)-hept-1-yl)-methyl)-sulfonyl)spiro-(1H)-indan-1,4'-piperidine In an oven dried flask under nitrogen were dissolved endo-(1S)-1'-(((2-amino-7,7-dimethylbicyclo(2,2,1)hept-1-y-1-)-methyl)-sulfonyl)spiro(1H-indan-1,4'-piperidine) (50 mg, 0.125 mmol), L-N-(tertbutoxycarbonyl)-glutamine (30.7 mg, 0.125 mmol) and benzotriazol-1-yloxytris(dimethylamino)phosphoniumhexafluorophosphate sequalog (55 mg, 0.125 mmol) in acetonitrile (3 mL). Diisoproplethylamine (100 µL) was added to make the solution basic. After HC(silicamethylenechloride (9)-methanol (1)) showed a new spot, the reaction mixture was concentrated to an oil. The oil was dissolved in methylenechloride-ether (1:3) and the solution was washed with sodium bicarbonate (saturated, aqueous), water, potassium hydrogen sulfate (10%) and salt (saturated, aqueous). The organic layer was dried with sodium sulfate. After filtration, the solution was concentrated to an oil which was purified by silica "flash" chromatography using methylenechloridemethanol (9:1) as solvents. The product fractions were concentrated to an oil. The addition of hexane:ether followed by concentration under reduced pressure gave the title compound as a white foam.

NMR (CDCl$_3$): Consistent with structure

HPLC: >79.5% pure

Elem. Anal Calc'd for $C_{33}H_{50}N_4O_6S \cdot 0.25\ H_2O$: Calc'd: C, 62.39; H, 8.01, N, 8.82. Found: C, 62.37; H, 7.99, N, 8.73.

Step 2:
Endo-(1S)-1'-(((2-L-(2-amino)glutaramylamino)-7,7-dimethylbicyclo(2.2.1)hep-1-yl)-methyl)-sulfonyl)-spiro(1H-indan-1,4'-piperidine)hydrochloride Endo-(1S)-1'-(((2-(L-2(tert.butoxycarbonylamino)-glutaramyl)amino-7,7dimethylbicyclo(2.2.1)-hept-1-yl)-methylsulfonyl)spiro(1H)-indan-1,4'-piperidine was dissolved in ethyl acetate (5 ml) and cooled to −5°. This solution was placed under a nitrogen atomosphere and hydrogen chloride gas was bubbled in for 10 minutes. The solvent was removed under reduced pressure. Ether was added and removed under reduced pressure to give the title compoud a white solid.

HPLC: >92%.

Mass Spectra: M+H @ 532.4 (Freebase).

NMR (CDCl$_3$) Consistent with structure.

Analysis for $C_{28}H_{42}N_4O_4S \cdot HCl \cdot 1.35H_2O \cdot 0.25$hexane: Cal'd: C, 57.79; H, 8.09; N, 9.14. Found: C, 57.80; H, 8.16; N, 9.14.

Step 3:
Endo-(1S)-1'-(((2-(L-2(4-imidazoleacetylamino)-glutaramyl)amino-7,7-dimethylbicyclo(2.2.1)hept-1-yl)-methyl)-sulfonyl)spiro(1H)indan-1,4'-piperidine)

In an oven dried flask (50 ml) under nitrogen was dissolved endo-(1S)-1'-(((2-L-(2-amino)-glutaramylamino-7,7-dimethylbicyclo(2.2.1)hept-1-yl)methyl)-sulfonyl)spiro(1H)-indan-1,4'-piperidine hydrochloride (56.7 mg, 0.0001 m), 4-imidazoleacetic acid hydrochloride (20 mg, 0.000124 m), 1-ethyl-3-(3-dimethylaminopropyl)carbodiimide hydrochloride (30 mg, 0.15 mmol) and 1-hydroxybenzotriazole hdyrate (20 mg, 0.15 mmol) in dimethylformamide (1 ml). Triethylamine (120 μl) was added to make the solution basic (pH-9). A white solid separated. After stirring for 18 hours, the solvent was removed under reduced pressure. The residue was dissolved in ether-methylene chloride (3:1). The cloudy solution was washed with sodium bicarbonate (sat., aqueous) and brine. After drying with sodium sulfate, the solution was filtered and concentrated to an oil. The product was purified by "flash" silica chromatography using methylene chloride:methanol (9:1) as solvent the product fractions, were collected and concentrated to give an oil. Ether-hexane were added and removed under reduced pressure to yield the title compound as a white foam.

HPLC: >94%.

Mass Spectra: M+H @ 639.6

NMR (CDCl$_3$) consistent with structure.

Analysis cal'd for $C_{33}H_{46}N_6O_5S \cdot 1.30H_2O$: Cal'd: C, 59.85; H, 7.40; N, 12.69. Found: C, 59.66; H, 7.36; N, 12.97.

EXAMPLE 11

Endo-(1S)-1'-(((2-(L-2(1-methyl-4-imidazoleacetylamino)glutaramyl)amino)-7,7-dimethyl-bicyclo(2.2.1)hept-1-yl)-methyl)-sulphonyl)spiro(1H-indan-1,4'-piperidine)

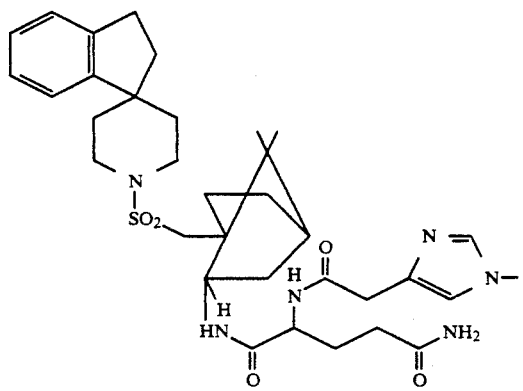

In an oven dried flask (50 ml) under nitrogen was dissolved endo-(1S)-1'-(((2-L-(2-amino)-glutaramylamino-7,7-dimethylbicyclo(2.2.1)hept-1-yl)-methyl)-sulfonyl)spiro(1H)-indan-1,4'-piperidine hydrochloride (57 mg, 0.1 mmol), 1-methyl-4-imidazole acetic acid hydrochloride (20 mg, 0.1 mmol), 1-ethyl-3-(3-dimethylaminopropyl)carbodiimide hydrochloride (30 mg, 0.15 mmol) and 1-hydroxybenzotriazole hydrate (20 mg, 0.15 mmol) in dimethylformamide (1 ml). Triethylamine (120 μl) was added to make the solution basic (pH 9). A white solid separated. After stirring for three days, the solvent was removed under reduced pressure. The residue was dissolved in ether:methylenechloride (3:1). The cloudy solution was washed with sodium bicarbonate (sat., aqueous) and brine. The organic layer was dried over sodium sulfate, filtered and concentrated to an oil. The product was isolated by "flash" silica chromatography using methylene chloride, methanol and ammonium hydroxide (9:1:1) as solvents. The product fractions were collected and concentrated to an oil. After adding ether:hexane and removing the solvents under reduced pressure, the title compound obtained as white foam.

HPLC: >90%.

Mass Spectra: M+H @ 653.3.

NMR (CDCl$_3$) consistent with structure.

Analysis for $C_{34}H_{48}N_6O_5S \cdot 1.55H_2O$: Cal'd: C, 59.98; H, 7.57; N, 12.35. Found: C, 60.00; H, 7.33; N, 12.05.

EXAMPLE 12

Endo-(1S)-1'-(((2-(L-2(β-alaninylamino)glutaramyl-)amino)-7,7-dimethylbicyclo(2.2.1)hept-1-yl)-methyl)-sulfonyl)spiro(1H)-indan-1,4'-piperidine

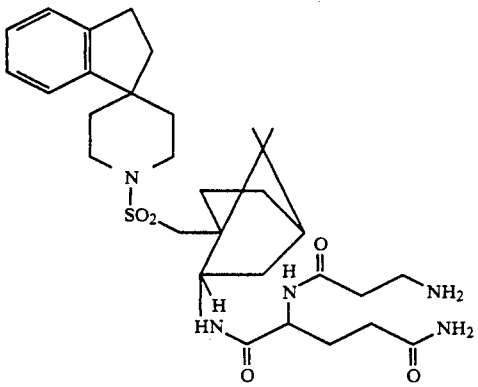

Step 1:
Endo-(1S)-1'-(((2-(L-2(βtert.butoxycarbonylaminoalaninylamino)glutaramyl)amino)-7,7-dimethylbicyclo(2.2.1)hept-1-yl)-methyl)-sulfonyl)-spiro(1H)-indan-1,4'-piperidine In an oven dried flask (50 ml) under nitrogen was dissolved endo-(1S)-1'-(((2-L-(2-amino)-glutaramylamino-7,7-dimethylbicyclo(2.2.1)hept-1-yl)methyl-sulfonyl)spiro-(1H)-indan-1,4'-piperidine hydrochloride (110 mg, 0.19 mmol), β-N-(tert.butoxycarbonyl)alanine (37.8 mg, 0.2 mmol), 1-ethyl-3-(3-dimethylaminopropyl)carbodiimide hydrochloride (60 mg, 0.3 mmol), and 1-hydroxybenzotriazole hydrate (40 mg, 0.0003 m) in dimethylformamide (2 ml). Triethylamine (120 μl) was added to make the solution basic (pH 9). A white solid separated. After stirring for 18 hours, the solvent was removed under reduced pressure. The residue was dissolved in ether:methylene chloride (3:1). The cloudy solution was washed with sodium bicarbonate (sat., aqueous), water, potassium hydrogen sulfate (10%, aqueous) and brine. The organic layer was dried over sodium sulfate, filtered and concentrated to an oil. The product was purified by "flash" silica gel chromatography using methylene chloride:methanol (9:1) as solvent. The product fractions were collected and concentrated to give an oil. After adding ether:hexane and removing it under reduced pressure, the title compound was obtained as a white foam.

HPLC: >98%.
Mass Spectra: M+H @ 702.4.
NMR (CDCl$_3$) consistent with structure.
Analysis for C$_{36}$H$_{55}$N$_5$O$_7$S: Cal'd: C, 61.60; H, 7.90; N, 9.98. Found: C, 61.51; H, 8.02; N, 9.62.

Step 2:
Endo-(1S)-1'-(((2-(L-2(βaminoalaninylamino)-glutaramyl)amino)-7,7-dimethylbicyclo(2.2.1)hept-1-yl)-methyl)-sulfonyl)spiro(1H)-indan1,4'-piperidine hydrochloride Endo-(1S)-1'-(((2-(L-2-(βtert.butoxycarbonylaminoalaninylamino)glutaramyl)amino-7,7-dimethylbicyclo(2.2.1)hept-1-yl)methyl-sulfonyl)spiro-(1H)indan-1,4'-piperidine was dissolved in ethylacetate (5 ml) and cooled to −5° C. This solution was placed under a nitrogen atmosphere and hydrogen chloride gas was bubbled in for 10 minutes. The solvent was removed under reduced pressure. Ether was added and removed under reduced pressure to give the title compound as a white foam.

HPLC: >97%.
Mass Spectra for free base M+H @ 602.3 (freebase).
NMR (CDCl$_3$) consistent with structure.
Analysis for C$_{31}$H$_{47}$N$_5$O$_5$S.HCl.1.30H$_2$O.0.25 ethylacetate: Cal'd: C, 56.21; H, 7.75; N, 10.24. Found: C, 56.23; H, 7.50; N, 10.24.

EXAMPLE 13

Endo-(1S)-1'-(((2-(L-2(methylamalonylamino)-glutaramyl)amino)-7,7-dimethylbicyclo(2.2.1)hept-1-yl)-methyl)sulfonyl)spiro(1H)-indan-1,4'-piperidine

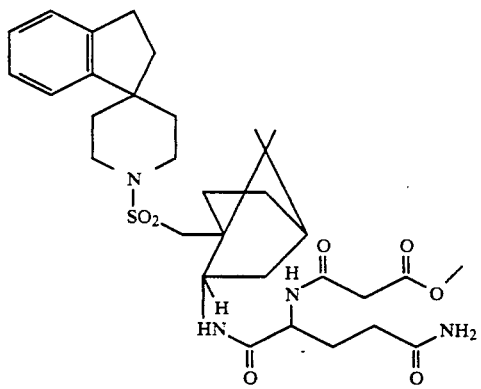

In an oven dried flask (50 ml) under nitrogen was dissolved endo-(1S)-1'-(((2-L-(amino)glutaramylamino-7,7-dimethylbicyclo(2.2.1)hept-1-yl)methyl)-sulfonyl-spiro(1H)-indan-1,4'-piperidinehydrochloride (56.7 mg, 0.1 mmol) in methylene chloride (3 ml). Monomethylmalonyl chloride (13.7 μl, 0.1 mmol) was added. After stirring 2 minutes, triethylamine (100 ml) was added to make the solution basic (pH 9). TLC (silica (methylenechloride)(methanol) (9:1) showed a new spot. The solvent was removed under reduced pressure. The gym was purified by "flash" silica gel chromatography using methylenechloride: methanol (9:1) as solvent. The title compound was isolated and concentrated to an oil which became a foam upon hexane-ether treatment.

HPLC: >95%.
Mass Spectra: M+H @ 631.5.
NMR (CDCl$_3$) consistent with structure.
Analysis for C$_{32}$H$_{46}$N$_4$O$_7$S.0.45H$_2$O: Cal'd: C, 60.15; H, 7.40; N, 8.77. Found: C, 60.15; H, 7.23; N, 8.78.

EXAMPLE 14

Endo-(1S)-1'-(((2-(L-2(2(methylsulfonyl)ethylamino)-glutaramy)amino-7,7-dimethylbicyclo(2,2,2)hept-1-yl)methyl)-sulfonyl)-spiro-(1H)-indan-(1,4')piperidine

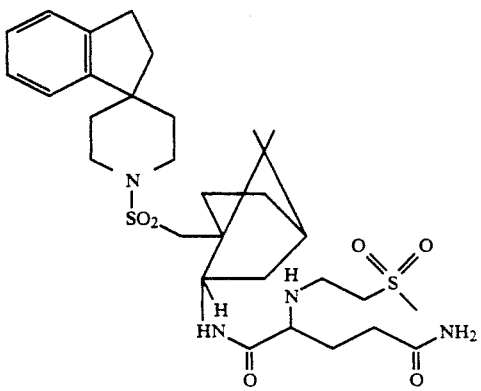

In an ovendried flask (50 mL) was dissolved endo-(1S)-1'-(((2-L-(amino)glutaramylamino-7,7-dimethyl-bicyclo(2,2,1)hept-1-yl)-methyl)-sulfonyl)spiro-(1H)indan-1,4'-piperdine hydrochloride (57 mg, 0.1 mmol) in methanol (2 mL). Methylvinyl sulfone (10 mg, 8.3 µL, 0.1 mmol) and triethylamine (20 µL) were added via syringe. It was necessaty to add more (2 µL) methylvinylsulfone after 2 hpurs. The reaction was stirred at room temperature overnight. The solvent was removed under reduced pressure to yield a gum. Purification was achieved by silica "flash" chromatography using methylene chloride:methanol (9:1) as solvents. The product fractions were collected and concentrated to give a gum. After adding ether-hexane and removing these solvents under reduced pressure, the title compound was isloated as a white foam.

HPLC: >94%.
Mass Spectra: M+H @ 637.3.
NMR (CDCl$_3$) consistent with structure.
Analysis for C$_{31}$H$_{48}$N$_4$O$_6$S$_2$.0.5H$_2$O: Cal'd: C, 57.64; H, 7.65; N, 8.68. Found: C, 57.67; H, 7.34; N, 8.96.

EXAMPLE 15

Endo-(1S)-1'-(((2-(L-2(4-imidazoleacetylamino)his-tidinyl)amino-7,7-dimethylbicyclo(2,2,2)hept-1-yl)me-thyl)-sulfonyl)spiro-(1H)-indan-1,4-piperdine

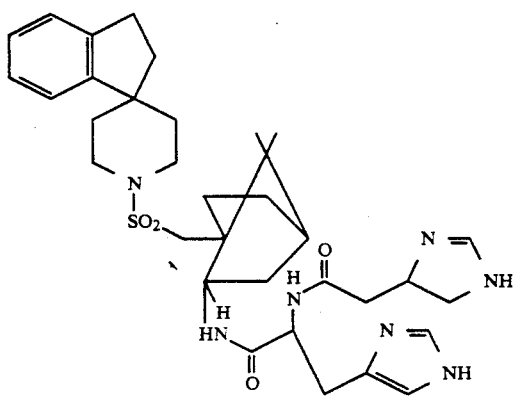

In an overdried flask (50 mL) under nitrogen was dissolved Endo-(1S)-1'-(((2-(L-N-histidinyl)amino7,7-dimethylbicyclo(2,2,1)hept-1-yl)-methyl)-sulfonyl)-spiro-(1H)-indan-1,4'-piperidinehydrochloride (20 mg, 0.124 mmol), 1-ethyl-3-(3dimethylaminopropyl)carbodiimidehydrochloride (30 mg, 0.15 mmol), and 1-hydroxybenxotriazolehydrate (20 mg, 0.15 mmol) in dimethylformaide (1 mL). Triethylamine (150 µL) was added to make the solution basic (pH 9). After stirring overnight, the solvent was removed under pressure. The product was isolated by "flash" silica gel chromatograph using methylenechloride-methanolammoniumhydroxide (9:1:1) as solvent. The product fractions were collected and concentrated to yield the title compound as a light tan foam.

HPLC: >97%,
Mass Spectra: M+H @ 648.3
NMR (CDCl$_3$) consistent with structure
Analysis for C$_{34}$H$_{45}$N$_7$O$_4$S.0.70H$_2$O.0.60 ethylether: Cal'd: C, 62.02; H, 7.49; N, 13.91. Found: C, 61.99; H, 7.34; N, 13.92:

EXAMPLE 16

Endo-(1S)-1'-(((2,2-(2(methylsulfone)ethyl)(1)-(1-methyl-4-imidazadeacetyl)amino-7,7-dimethylbicyclo(2,2,1-)hept-1-yl)-methyl)-sulfonyl)spiro-(1H)-indan-1,4'-piperidine

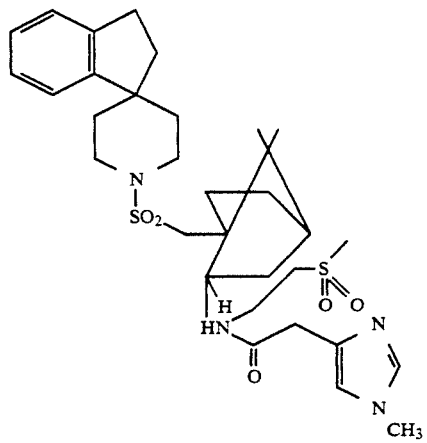

Step 1:
Endo-(1S)-1'-(((2-2-(methylsulfonyl)ethyl)amino-7,7-dimethylbicyclo(2,2,1)hept-1-yl)methyl)-sulfonyl)spiro-(1H)-indan-1,4'-piperidine A solution of Endo-(1S)-1'(((2 amino-7,7dimethyl-bicyclo(2,2,1)hept-1-yl)-methyl)-sulfonyl)spiro-(1H)-indan-1,4'-piperdine (100 mg, 0.25 mmol) and methylvinylsulfone (22 mg, 20.5 µL, 0.22 mmol) in methanol (2 mL) in a 20 mL flask was stirred overnight. The solvent was removed under reduced pressure. The product was isolated by "flash" chromatography using methylenechloride:methanol (9:1) as solvent. The product fractions were collected and concentrated. Upon treatment with hexane:ether, the title compound was obtained as a white foam.

HPLC: >99%
Mass Spectra: M+H @ 509.2
NMR (CDCl$_3$) consistent with structure,
Analysis for C$_{26}$H$_{40}$N$_2$O$_4$S.0.25H$_2$O: Cal'd: C, 60.84; H, 7.95; N, 5.46. Found: C, 60.79; H, 7.78; N, 5.55.

Step 2

In an ovendried flask (50 mL) under nitrogen was dissolved endo-(1S)-1'-(((2-2-(methylsulfonyl)ethyl-)amino-7,7-dimethylbicyclo(2,2,1)hept-1-yl)methyl)-sulfonyl)spiro-(1H)-indan-1,4'-piperdine (50 mg, 0.1 mmol), 1-methyl-4-imidazole acetic acid hydrocloride (20 mg, 0.1 mmol), 1-ethyl-3-(3dimethylaminopropyl)-carbodiimide hydrochloride (30 mg, 0.15 mmol) and 1-hydroxybenztriazolehydrate (20 mg, 0.15 mmol) in dimethylformamide (1 mL). A white solid separated after triethylamine (100 μL) was added to make the solution basic (pH 9). After stirring overnight, the solvent was removed under reduced pressure. The oil was dissolved in ether-methylene chloride (3:1). The cloudy solution was washed with sodium bicarbonate (saturated, aqueous), water, potassium hydrogen sulfate (10%, aqueous) and brine. The organic layer was dried over sodium sulfate, filtered and concentrated to an oil. The product was obtained by "flash" chromatography using methylenechloride, methanol, ammoniumhydroxide (9:1:1) as solvent. The product fractions were collected and concentrated. After adding ether:hexane and removing these solvent, the title compound was obtained as a white foam.

HPLC: >98%.

Mass Spectra: M+H @ 631.3.

NMR (CDCl$_3$) consistent with structure.

Analysis for C$_{32}$H$_{46}$N$_4$O$_5$S$_2$.1.30H$_2$O: Cal'd: C, 58.74; H, 7.49; N, 8.56. Found: C, 58.72; H, 7.10; N, 8.41.

EXAMPLE 17

Endo-(1S)-1'-(((2-(2(N-butoxycarbonyl-piperidine)acetyl)amino-7,7-dimethylbicyclo(2,2,1-)hept-1-yl)-methyl)sulfonyl)spiro-(1H)-indan-1,4'-piperidine

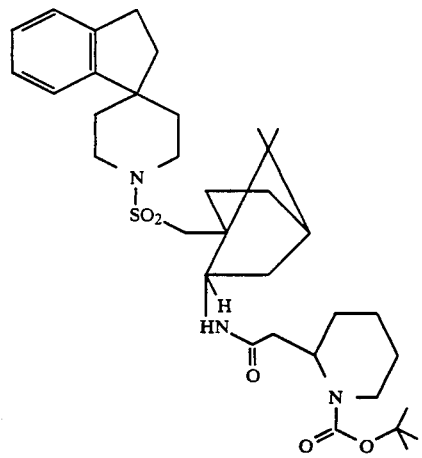

In an overdried flask (50 mL) under nitrogen was dissolved endo-(1S)-1'-(((2-amino-7,7-dimethylbicyclo(2,2,1)hept-1-yl)-methyl)-sulfonyl)spiro-(1H)indan-1,4'-piperdine (50 mg. 0.125 mmol), 2-(N-tert.butoxycarbonylpiperidine)acetic acid (40 mg, 0.16 mmol), 1-ethyl-3-(3di-methylaminopropyl)carbodiimidehydrochloride (30 mg, 0.15 mmol), and 1-hydroxy-benztriazolehydrate (20 mg. 0.15 mmol) in dimethylformanide (1 mL). Triethylamine (50 μL) was added to make the solution basic (pH 9). After one hour, the solvent was removed under pressure and the residue was dissolved in ether:methylenechloride (3:1). The organic solution was washed with sodium bicarbonate (saturated, aqueous), water, potassium hydtogen sulfate (10% aqueous) and brine. The solution was dried over sodium sulfate, filtered and concentrated to an oil. The product was purified by "flash" chromatography using methylenechloride:methanol (9:1) as solvnets. The product fractions were collected and concentrated. The addition and removal of hexane:ether gave the title compound as a white foam.

HPLC: >96%.

Mass Spectra: M+H @ 685.5.

NMR (CDCl$_3$) consistent with structure.

Analysis for C$_{37}$H$_{56}$N$_4$O$_6$S.0.3H$_2$O: Cal'd: C, 64.37; H, 8.26; N, 8.12. Found: C, 64.37; H, 8.13; N, 8.12.

EXAMPLE 18

Endo-(1S)-1'-(((2-(dimethylaminoglycinylglycinyl-)amino-7,7-dimethylbicyclo(2,2,1)hept-1-yl)-methyl)-sulfonyl)spiro-(1H)-indan-1,4')-piperidine

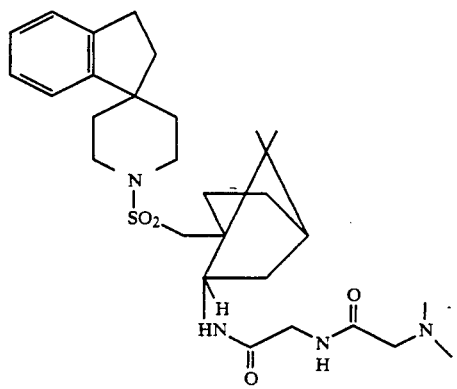

Step 1:

Endo-(1S)-1'-(((2-(tertbutoxycarbonylglycinylglycinyl-)amino-7,7dimethylbicyclo(2,2,1)hept-1-yl)-methyl)-sulfonyl)spiro-(1H)-indan-1,4'-piperidine Into an overdried falsk (50 mL) under nitrogen was placed dimethylformadide (1 mL). Endo-(1S)-1'-(((2amino-7,7-dimethylbicyclo(2,2,1)hept-1-yl)-methyl)sulfonyl)spiro-(1H)-indan-1,4'-piperidine (50 mg, 0.125 mmol), N-tertbutoxycarbonylglycinylglycine (29 mg, 0.125 mmol), 1-ethyl-3-(3dimethylaminopropyl)carbodiimide-hydrochloride (30 mg, 0.15 mmol) and 1-hydroxybenztriazolehydrate (20 mg, 0.15 mmol) were introduced and the mixture was stirred until solution occurred. Triethylamine (50 μL) was added and white solid separated. After 1 hour, the reaction was completed and the solvent was removed by reduced pressure. The gummy residue was dissolved in ether:-methylene chloride (3:1). The cloudy solution was washed with sodiumbicarbonate (saturated, aqueous), water, potassiumhydrogensulfate, (10%, aqueous) and brine. The organics were dried over sodium sulfate, filtered and concentrated to an oil. The product was isolated by silica gel "flash" chromatograohy using methylenechloride:methanol (9:1) as solvent. The product fractions were collected and concnetrated to an oil. Ether-hexane was added and was removed under reduced pressure to yield the title compound as a foam.

HPLC: >98%

Mass Spectra: M+H @617

NMR (CDCl$_3$) consistent with structure

Analysis for $C_{32}H_{48}N_4O_6S.0.3$ hexane Cal'd: C, 63.30; H, 8.24; N, 8.66. Found: C, 63.26; H, 8.26; N, 8.84.

Step 2:
Endo-(1S)-1'-(((2-(glycinylglycinyl)amino7,7-dimethylbicyclo(2,2,1)hept-1-yl)-methyl)sulfonyl)spiro-(1H)-indan-(2,4')-piperidine hydrochloride Endo-(1S)-1'-(((2-(tertbutoxycarbonylglycinylglycinyl)amino-7,7dimethylbicyclo(2,2,1)hept-1-yl)methyl)-sulfonyl)spiro-(1H)-indan-1,4'-piperidine was dissolved in ethyl acetate (5 mL) and cooled to $-5°$ C. This was placed under an atmosphere of nitrogen and hydrogen chloride gas was bubbled in for 10 minutes. The solvent was removed under reduced pressure. Ether-hexane was added and then removed under reduced pressure to yield the title compound as a white foam.

HPLC: >98%.
Mass Spectra: M+H @ 517.3 (Freebase).
NMR (CDCl$_3$) consistent with structure.
Analysis for $C_{27}H_{40}N_4O_4S.HCl.0.80\ H_2O$. 0.25 ethylacetate. Cal'd: C, 57.03; H, 7.62; N, 9.50. Found: C, 57.06; H, 7.35; N, 9.68.

Step 3

Endo-(1S)-1'-(((2-(glycinylglycinyl)amino-7,7-dimethylbicyclo(2,2,1)hept-1-yl)-methyl)-sulfonyl)spiro-(1H)-indan-(2,4')-piperidine hydrochloride was dissolved in 1% acetic acid/methanol (3 mL). Formaldehyde (50 μL, 37% aqueous) was added followed by sodium cyanoborohydride (20 mG). After stirring overnight, the reaction mixture was cooled to 0° and sodium bicarbonate (10 mL, saturated, aqueous) was added. The resulting suspension was extracted with ethyl acetate. The ethyl acetate was washed with brine and was dried over sodium sulfate. After filtration and concentration, the oil was purified by "flash" chromatography using methylenechloride-methanol (9:1). The product fractions were concentrated and then ether-hexane was added and was removed to yield the title compound as a foam.

HPLC: >96%.
Mass Spectra: M+H @ 545.4
NMR (CDCl$_3$) consistent with structure
Analysis for $C_{29}H_{44}N_4O_4S.0.95\ H_2O$: Cal'd: C, 61.99; H, 8.23; N, 9.87. Found: C, 62.00; H, 7.90; N, 9.85.

EXAMPLE 19

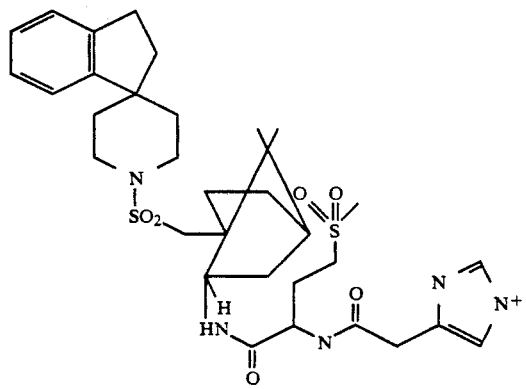

2-Amino-N-[1-[[(2,3-dihydrospiro[1H-indene1,4'-piperidin]-1'-yl)sulfonyl]methyl]-7,7-dimethylbicyclo[2.2.1]hept-2-yl]-4-(methylsulfonyl)-butanamide hydrochloride (150 mg, 0.265 mmole) and 4-imidazolecarboxilic acid (49 mg, 0.304 mmole) were combined with 61 mg (0.318 mmole) of 1-ethyl-3-(3-dimethylaminopropyl)carbodiimide hydrochloride and 43 mg (0.318 mmole) of 1-hydroxybenzotriazole in 12 ml of dry N,N'-dimethylformamide at room temperature under nitrogen. The pH of the reaction mixture was adjusted to 9 with triethylamine and the resulting solution was stirred for 6 hours. An additional 0.5 equivalent each of imidazolecarboxilic acid, 1-ethyl-3-(3-dimethylaminopropyl)carbodiimide hydrochloride, and 1-hydroxybenzotriazole were added and stirring was continued for 48 hours more. The reaction mixture was diluted with methylene chloride (150 ml) and the resulting solution was washed with saturated sodium bicarbonate solution (2×40 ml), 10% citric acid solution (2×40 ml), and brine, then dried (magnesium sulfate) and concentrated to give 100 mg of crude product. The crude product was dissolved in methanol and filtered through glass wool. The filtrate was purified via preparative HPLC chromatography employing a Vydac C-18 column (4.5×150 mm, water-acetonitrile-1% trifluoroacetic acid 45 minute gradient). The homogeneous fractions containing product were pooled and concentrated. The residue was dissolved in ethyl acetate from which the title compound precipitated as a white, amorphous solid:

NMR: Consistent with structure;
HPLC: >99% pure at 214 nm;
FAB MS: 674 (M$^+$ +H);
Elem. Anal. calc'd for $C_{33}H_{47}N_5O_6S_2.1.0$ trifluoroacetic acid: Calc'd: C, 53.35; H, 6.14; N, 8.89. Found: C, 53.16; H, 6.04; N, 8.89.

EXAMPLE 20

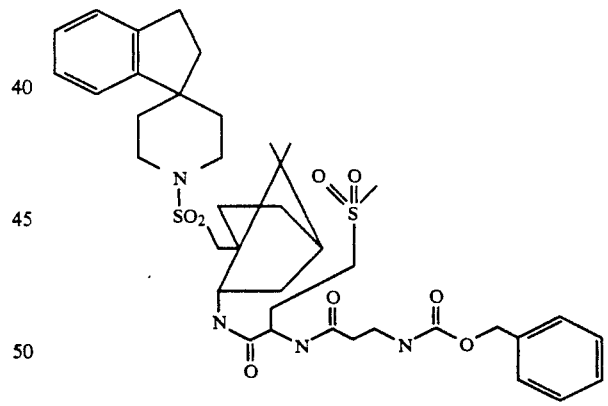

2-Amino-N-[1-[[(2,3-dihydrospiro[1H-indene-1,4'-piperidin]-1'-yl)sulfonyl]methyl]-7,7-dimethylbicyclo[2.2.1]hept-2-yl]-4-(methylsulfonyl)-butanamide hydrochloride (150 mg, 0.265 mmole) was suspended in 5 ml of methylene chloride. The pH of the suspension was adjusted to 9 with triethylamine. To this homogeneous solution was then added benzyloxycarbonyl-b-alanine (71 mg, 0.398 mmole), 1-ethyl-3-(3-dimethylaminopropyl)carbodiimide hydrochloride (86 mg, 0.450 mmole), and 1-hydroxybenzotriazole (61 mg, 0.450 mmole), respectively. The reaction mixture was stirred at room temperature under nitrogen for 24 hours. The reaction mixture was concentrated under reduced pressure and the residue was partitioned between ethyl acetate (100 ml) and sodium bicarbonate solution. The phases were separated and the organic phase was washed with saturated sodium bicarbonate solution (3×40 ml), 10% citric acid solution, and brine, then dried (magnesium sulfate) and concentrated to give 200 mg of a solid. Recrystallization from methanol gave the analytical sample as a white amorphous solid:

NMR: Consistent with structure;
HPLC: >99% pure at 214 nm;
FAB MS: 771 (M+ +H);
Elem. Anal. calc'd for $C_{39}H_{53}N_4O_8S_2$: Calc'd: C, 60.83; H, 6.94; N, 7.27. Found: C, 60.59; H, 7.01; N, 7.34.

EXAMPLE 21

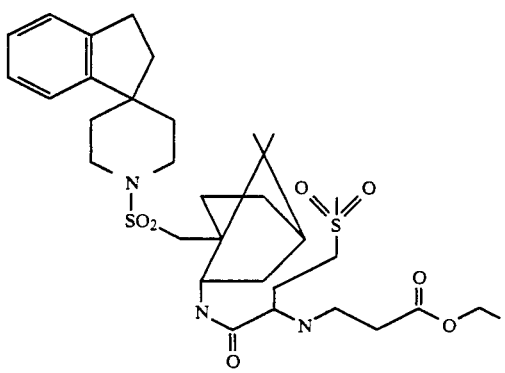

2-Amino-N-[1-[[(2,3-dihydrospiro[1H-indene-1,4'-piperidin]-1'-yl)sulfonyl]methyl]-7,7-dimethylbicyclo[2.2.1]hept-2-yl]-4-(methylsulfonyl)-butanamide hydrochloride (150 mg, 0.265 mmole) was suspended in 2.5 ml of methanol and treated with a solution of 2.65 ml of ethylacrylate in 2.5 ml of methanol. The pH of the reaction mixture was adjusted to neutrality with the addition of one equivalent of triethylamine. The reaction mixture was then stirred at room temperature for 24 hours. The reaction mixture was concentrated under reduced pressure and the residue was partitioned betweeb ethyl acetate (100 ml) and water. The phases were separated and the organic phase was washed with water and brine, then dried (magnesium sulfate) and concentrated to give 80 mg of an oil. This material was purified via preparative thick layer chromatography on silica gel (chloroform-methanol development, 96:4, v/v; 10% methanol-tetrahydrofuran isolation from silica gel) to give a white solid which was crystallized from methanol:

NMR: Consistent with structure and confirms presence of solvent;
HPLC: >98% pure at 214 nm;
FAB MS: 666 (M+ +H);
Elem. Anal. calc'd for $C_{33}H_{51}N_3O_7S_2.1.1$ tetrahydrofuran: Calc'd: C, 60.27; H, 8.09; N, 5.64. Found: C, 60.28; H, 7.89; N, 5.34.

EXAMPLE 22

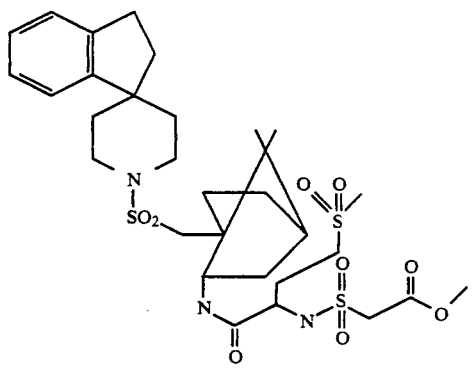

2-Amino-N-[1-[[(2,3-dihydrospiro[1H-indene-1,4'-piperidin]-1'-yl)sulfonyl]methyl]-7,7-dimethylbicyclo[2.2.1]hept-2-yl]-4-(methylsulfonyl)-butanamide hydrochloride (100 mg, 0.176 mmole) eas suspended in 5 ml of methylene chloride and was treated in succession with methylchlorosulfonyl acetate (45 mg) and sufficient triethylamine to ring the pH of the reaction mixture to approximately 10. The reaction mixture was protected from moisture and stirred at room temperature for 18 hours. Another equivalent of methylchlorosulfonyl acetate was added and stirring was continued for six hours more. The reaction mixture was concentrated under reduced pressure and the residue was partitioned between ethyl acetate (100 ml) and water. The phases were separated and the organic phase was washed with water and brine, then dried (magnesium sulfate) and concentrated to give 102 mg of crude product as a solid, This material was purified via flash column chromatography on silica gel (chloroformmethanol development, 98:2, v/v) to give 94 mg of a solid. Rechromatography on silica gel (chlorofrom-methanol development, 96:4, v/v) and trituration with ether-petroleum ether gave the analytical material:

NMR: Consistent with structure;
HPLC: >95% pure at 214 nm;
FAB MS: 702 (M+ +H); Elem. Anal. calc'd for $C_{31}H_{47}N_3O_9S_3$: Calc'd: C, 53.04; H, 6.74; N, 5.99. Found: C, 52.95; H, 6.91; N, 5.80.

EXAMPLE 23

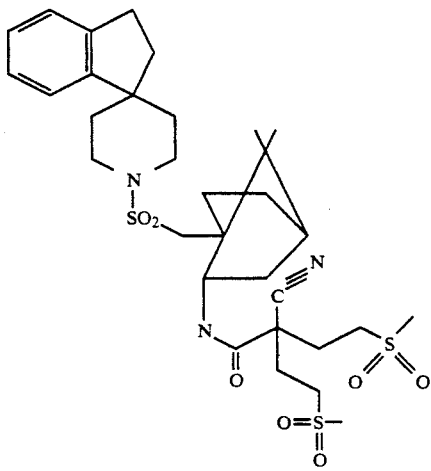

2-[1-[[(2,3-dihydrospiro[1H-indene-1,4'-piperidin]-1'-yl)sulfonyl]methyl]-7,7-dimethylbicyclo[2.2.1]hept-2-yl]cyanoacetamide (108 mg, 0.230 mmole) was combined with methylvinylsulfone (29 mg, 0.272 mmole) and 0.5 ml of 1,8-diazabicyclo[5.4.0]undec-7-ene in 8 ml of tetrahydrofuran. The reaction mixture was protected from moisture and heated to reflux for 23 hours. The reaction mixture was concentrated under reduced pressure and the residue was partitioned between ethyl acetate (100 ml) and water. The phases were separated and the organic phase was washed with saturated sodium bicarbonate solution (3×50 ml), 10% citric acid solution (1×50 ml), and brine. The dried (magnesium sulfate) organic extracts were concentrated to give 100 mg of crude product as a solid. This material was purified via flash column chromatography on silica gel (hexane-ethyl acetate, 1:2 v/v) to give the title compound as a white solid:

NMR: Consistent with structure and verifies presence of solvent:

HPLC: >99% pure at 214 nm;

FAB MS: 682 (M++H);

Elem. Anal. calc'd for $C_{32}H_{47}N_3O_7S_3 \cdot 0.8H_2O$: Calc'd: C, 55.21; H, 7.04; N, 6.03. Found: C, 55.21; H, 6.81; N, 5.82.

EXAMPLE 24

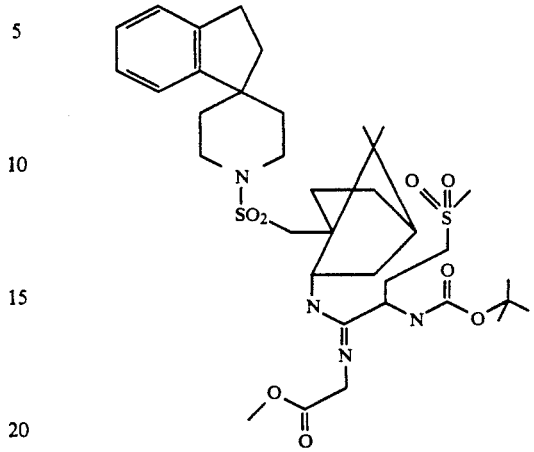

2-tert-Butyloxycarbonylamino-N-[1-[[(2,3-dihydrospiro[1H-indene-1,4'-piperidin]-1'yl)sulfonyl]methyl]-7,7-dimethylbicyclo[2,2,1]hept-2-yl]-4-(methylsulfonyl)-thiobutanamide (150 mg, 0.220 mmole) was conmbined with methylglycinate hydrochloride (21 mg, 0.242 mmole) and mercuric chloride (242 mmole) in a dtry 1:1 N,N-dimethylformamide-tetrahydrofuran solvent mixture. The pH of the reaction mixture was raised to 11 with triethylamine and the misture was heated at 60° C. overnight. The reaction mixture was concentrated under reduced pressure and the residue was partitioned between ethyl acetate (100 mL) and water. The phases were separated and the organic phase was washed with saturated sodium bicarbonete solution (3×50 mL) and brine. The dried (magnesium sulfate) organic extracts were concentrated to give the crude product as s bright red solid. This material was purified vis flash column chromatography on silica gel (chloroform-methanol-concentrated ammonium hydroxide elution, 90:10:1 v/v) to give 75 mg of the title compound as a yellow solid:

NMR: Consistent with structure and verifies presence of solvent:

HPLC: >97% pure at 214 nm; FAB MS: 682 (M++H);

Elem Anal calc'd for $C_{36}H_{56}N_4O_8S_2 \cdot 1.2H_2O \cdot 0.05HCl_3$: Calc'd: C, 56.63; H, 7.71; N, 7.33. Found: C, 56.26; H, 7.35; N, 7.76.

EXAMPLE 25

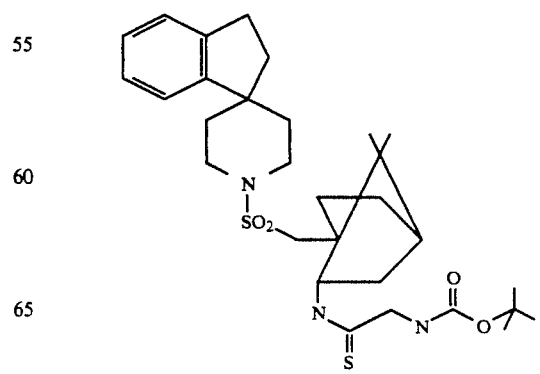

2-tert-Butyloxycarbonylamino-N-[1-[[(2,3-dihydrospiro[1H-indene-1,4'-piperidin]-1'yl)sulfonyl]methyl]-7,7-dimethylbicyclo[2,2,1]hept-2-yl]-acetamide (1.3 g, 2.48 mmole) was dissolved in 15 mL of tetrahydtofuran and treated with 752 mg (1.86 mmole) of Lawesson's reagent. The reaction mixture was heated to reflux for two hours and then concentrated in vacuo. The pH of the reaction mixture was reaised to 11 with triethylamine and the mixture was heated at 60° C. overnight. The reaction mixture was concentrated under reduced pressure and a portion of the residue was purified to homogeneity by preparative thick layer chromatography on silica gel (hexame-ethyl acetate, 7:3 v/v elution). The title compound was obtained as a white solid agter trituration with ether-petroleum ether:
NMR: Consistent with structure
HPLC:>97% pure at 214 nm;
FAB MS: 576 (M+ +H);
Elem Anal calc'd for $C_{30}H_{45}N_3O_4S_2$ Calc'd: C, 62.57; H, 7.87; N, 7.29. Found: C, 62.79; H, 8.09; N, 7.00.

EXAMPLE 26

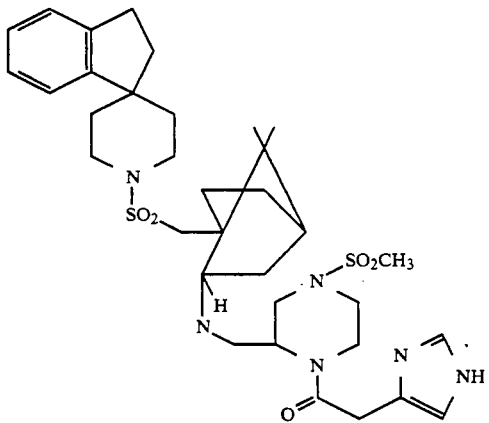

To a stirred solution of endo-(1S)-1'(((2-amino-7,7-dimethylbicyclo(2.2.1)-hept-1-yl)-methyl)-sulfonyl)-spiro(1H-indan-1,4'-piperidine (403 mg; 1 mmol) and 1-Fmoc-4-Cbz-2-piperazine carboxylic acid (535 mg; 1.1 mmol) in acetonitrile (8 mL), was added benzotriazol-1-yloxytris(dimethylamino)phosphonium hexafluorophosphate (487 mg; 1.1 mmol). Diisopropylethyl amine was added until pH−9. After stirring at room temperature for 15 hr the solution was concentrated then redissolved in ethyl acetate and washed successively with water, 1M HCl, and brine. The organic extract was dried over anhydrous magnesium sulfate, then concentrated under reduced pressure. The product was purified by flash chromatography (99:1 $CH_2Cl_2:CH_3OH$) to yield 860 mg of the product as a white foam (46%).

To a solution containing the product described above (400 mg; 0.46 mmol) in ethanol (100 mL) was added 10% Pd/C (50 mg). The mixture was attached to a Parr hydrogenator, and shaken at 60 psi. After 15 hr, the mixture was filtered and concentrated. A white foam (170 mg; 50%) was obtained by purification of the residue using flash chromatography (95:5 $CH_2Cl_2:CH_3OH$). A portion of this material (150 mg; 0.20 mmol) and diisopropylethyl amine (28 mg; 0.22 mmol) were dissolved in methylene chloride (4 mL) at 0° C. Methane sulfonyl chloride (25 mg; 0.22 mmol) was added. After stirring at room temperature for approximately 18 hr, piperidine (2 mL) was added. After an additional 2 hr the cloudy reaction mixture was filtered then concentrated under reduced pressure. Purification by flash chromatography (95:5 $CH_2Cl_2:CH_3OH$) yielded a white foam (108 mg; 91%).

To a solution of the product described above (81 mg; 0.132 mmol), 2-imidazoleacetic acid (27 mg; 0.164 mmol), and BOP reagent (73 mg; 0.164 mmol) in 3:1 acetonitrile:dimethylformamide (4 mL) was added diisopropylethyl amine until pH−8. After approximately 18 hr the dark solution was concentrated under reduced pressure. The title compound was obtained through purification of the residue by preparative HPLC (Vydac C18 reverse phase column; 1"×10"; gradient from 95:5 to 20:80 $H_2O:CH_3CN$ with 0.1% TFA; 10 mL/min flow rate; 60 min gradient). Lyophylization of the pure product from 1,4-dioxane gave a white solid (8 mg; 8%)

Anal. $(C_{34}H_{48}N_6O_6S_2).1.40$ TFA: Calc., C, 51.36; H, 5.79; N, 9.77. Found, C, 51.42; H, 5.71; N, 9.53.
HPLC: 100%.
$^1$HNMR: Consistent with structure.
FABMS: 701 (M+ +H).

EXAMPLE 27

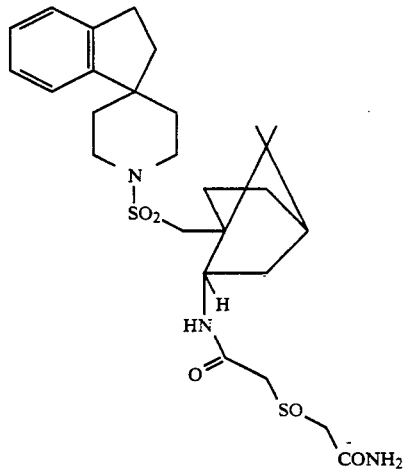

Step A

To a stirred solution of endo-(1S)-1'(((2-amino-7,7-dimethylbicyclo(2.2.1)-hept-1-yl)-methyl)-sulfonyl)-spiro(1H-indan-1,4'-piperidine (906 mg; 2.25 mmol) and diisopropylethyl amine (291 mg; 2.25 mmol) in methylene chloride (9 mL) at 0° C., was added a solution of 2-bromoacetyl bromide (453 mg; 2.25 mmol) in methylene chloride. The solution was allowed to warm to room temperature over 3 hr, then concentrated under reduced pressure. The product was purified by flash chromatography (9:1 methylene chloride:diethyl ether) to yield 1.1 g of a white foam (93%).

To a stirred solution containing 131 mg of the bromide described above (0.25 mmol) in ethyl alcohol (1 mL) was added diisopropylethyl amine (38.8 mg; 0.30 mmol) and ethyl-2-mercaptoacetate (36.1 mg; 0.30 mmol). After 2 hr, the solution was directly applied to a Vydac C18 reverse phase HPLC column (1"×10"; gradient from 95:5 to 30:70 $H_2O:CH_3CN$ with 0.1% TFA; 10 mL/min flow rate; 60 min gradient). The pure fractions were concentrated, then lyophylized from 1,4-dioxane to yield the title compound as a white solid (108 mg; 77%).

Anal.:(C29H42N2O5S2).0.15 TFA: Calc. C, 60.68; H, 7.33; N, 4.83. Found C, 60.76; H, 7.38; N, 5.03.

TLC: $R_f$=0.40 (98:2 CH2Cl2:CH3OH).
HPLC: 94.8%.
1HNMR: Consistent with structure.
FABMS: 563 (M+ +H).

Step B

The sulfide described in step A (113 mg; 0.20 mmol) was dissolved in methylene chloride (1.5 mL) and cooled to 0° C. meta-Chloroperbenzoic acid (40.6 mg; 0.20 mmol assuming 85% purity) was added, then the solution was allowed to warm to room temperature. After 1.5 hr the solution was concentrated. The residue was purified by preparative HPLC (Vydac C18 reverse phase column; 1"×10"; gradient from 95:5 to 20:80 H2O:CH3CN with 0.1% TFA; 13.5 mL/min flow rate; 60 min gradient). After lyophylization from 1,4-dioxane the title compound was obtained as a white solid (24 mg; 20%).

Anal. (C29H42N2O6S2).0.20 TFA: Calc. C, 58.69; H, 7.07; N, 4.66. Found C, 58.78; H, 7.13; N, 4.95.

HPLC: 98.9%.
1HNMR: Consistent with structure.
FABMS: 579 (M+ +H).

Step C

To a stirred solution of the product from step B (25 mg; 0.04 mmol) in ethyl alcohol (1 mL) at 0° C., was introduced a stream of ammonia gas. After 10 min, the reaction vessel was sealed and the solution was allowed to warm to room temperature. After 15 hr, the solution was concentrated, and the residue was purified by preparative HPLC (Vydac C18 reverse phase column; 1"×10"; gradient from 95:5 to 20:80 H2O:CH3CN with 0.1% TFA; 13.5 mL/min flow rate; 60 min gradient). After lyophylization from 1,4-dioxane the title compound was obtained as a white solid (22 mg; 92%).

Anal. (C27H39N3O5S2).0.45 TFA: Calc. C, 55.75; H, 6.62; N, 6.99. Found C, 55.60; H, 6.62; N, 6.77.

HPLC: 97%.
1HNMR: Consistent with structure.

FABMS: 550 (M+ +H).

EXAMPLE 28

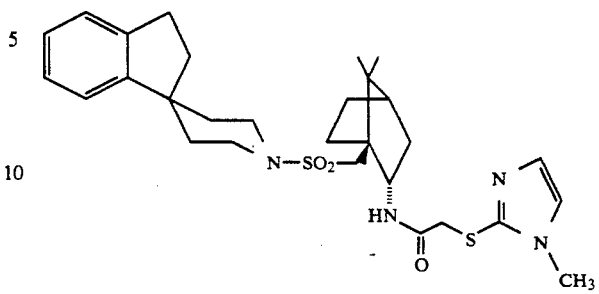

To a stirred solution of endo-(1S)-1'(((2-amino-7,7-dimethylbicyclo(2.2.1)-hept-1-yl)-methyl)sulfonyl)-spiro(1H-indan-1,4'-piperidine (300 mg; 0.745 mmol) in methylene chloride (25 mL) was added 2-bromoacetyl chloride (68—L; 0.82 mmol) followed by diisopropylethyl amine (130—L; 0.745 mmol). After 15 min at room temperature, the solution was concentrated under reduced pressure. Purification by flash chromatography (30% ethyl acetate in petroleum ether) afforded a white foam (362 mg; 93%). A portion of this material (100 mg; 0.203 mmol) was dissolved in absolute ethanol (20 mL) and placed into a flask equipped with a reflux condenser. Diisopropylethyl amine (106—L; 0.609 mmol) was added, followed by 2-mercapto-1-methylimidazole (70 mg; 0.609 mmol), then the temperature was increased to reflux. After approximately 18 hr the solution was cooled, then concentrated. Purification by flash chromatography (30% ethyl acetate in petroleum ether) provided 98 mg of the title compound as a white foam (87%).

Anal: (C29H40N4O3S2).0.14 CH2Cl2: Calc. C, 61.36; H, 7.12; N, 9.82. Found C, 61.38; H, 7.03; N, 9.94.

HPLC: (Vydac C18 Column; gradient from 95/5 to 0/100 H2O/CH3CN with 0.1% TFA. 15 min. gradient, flow rate=1.5 ml/min.) $R_t$=12.8 min. Purity=100%.

1HNMR: Consistent with structure
FABMS: m/z=557 (M+ +H)

EXAMPLE 29

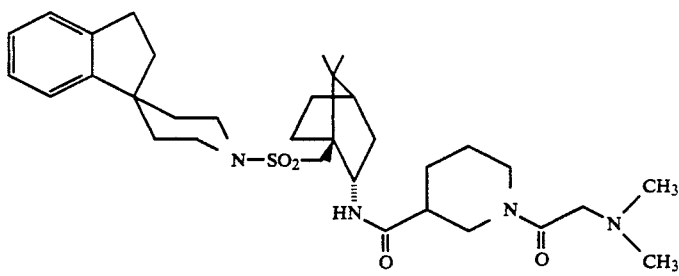

To a solution of endo-(1S)-1'(((2-amino-7,7-dimethylbicyclo(2.2.1)-hept-1-yl)-methyl)-sulfonyl)-spiro(1H-indan-1,4'-piperidine (801 mg; 1.99 mmol) in ethyl acetate (150 mL) was added 1-Fmoc-(DL)nipecotic acid (701 mg; 1.99 mmol), 1-hydroxybenzotriazole (269 mg; 1.99 mmol), and 1-(3-dimethylaminopropyl)-3-ethylcarbodiimide (496 mg; 2.59 mmol). After stirring at room temperature for 18 hr, the solution was washed successively with equal volumes of 1M NaOH, 1M HCl, and brine, dried over sodium sulfate then filtered and concentrated. Purification by flash chromatography (gradient from 30% ethyl acetate in petroleum ether to 50% ethyl acetate in petroleum ether) afforded a white foam (1.18 g; 81%) which was then dissolved in diethyl amine (20 mL). After 4 hr the solution was concentrated under reduced pressure. Purification by flash chromatography (gradient from 70% ethyl acetate in petroleum ether to 25% methanol in methylene chloride) afforded the intermediate as a white foam (722 mg; 87%). A portion of the foam (30 mg; 0.058 mmol) was dissolved in methylene chloride (12 mL). N,N-dimethyl glycine (10 mg; 0.070 mmol) was added, followed by 1-hydroxybenzotriazole (9.5 mg; 0.070 mmol), and 1-(3-dimethylaminopropyl)-3-ethylcarbodiimide (14 mg; 0.075 mmol). After 5 hr the mixture was concentrated, then partitioned between ethyl acetate (15 mL) and 1M NaOH (15 mL). The ethyl acetate solution was washed with brine, dried over sodium sulfate, then concentrated. Purification by preparative HPLC afforded after lyophylization from 1,4-dioxane, 11 mg of the title compound as an amorphous solid (32%).

Anal: $(C_{33}H_{50}N_4O_4S).1.88$ TFA: Calc. C, 54.29; H, 6.43; N, 6.89. Found C, 54.32; H, 6.62; N, 6.68.

HPLC: (Vydac C18 Column; gradient from 95/5 to 0/100 $H_2O/CH_3CN$ with 0.1% TFA. 15 min. gradient, flow rate=1.5 ml/min.) $R_t$=12.04 min. Purity=100%.

$^1$HNMR: Consistent with structure.

FABMS: m/z=599 (M+ +H).

EXAMPLE 30

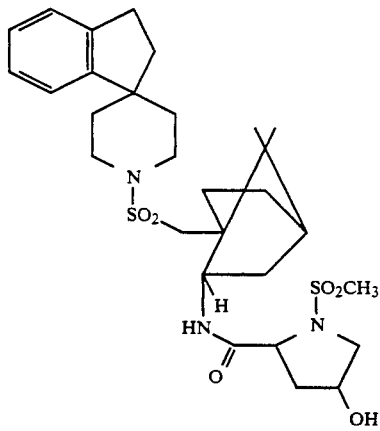

To a solution of endo-(1S)-1'-(((2-(L-4-hydroxyprolinoylamino)-7,7-dimethylbicyclo(2.2.1)hept-1-yl)-methyl)-sulfonyl)spiro(1H-indan-1,4-piperidine) hydrochloride (114 mg; 0.206 mmol) in dry tetrahydrofuran (20 mL) under $N_2$ was added methanesulfonyl chloride (24 mL; 0.310 mmol) and pyridine (20 mL; 0.248 mmol). After 4 hr at room temperature the solution was concentrated then partitioned between ethyl acetate (100 mL) and 1M HCl (100 mL). The ethyl acetate layer was dried over sodium sulfate, then concentrated. Purification by flash chromatography (10% methanol in methylene chloride) affored the title compound (81 mg).

Anal: $(C_{29}H_{43}N_3O_6S_2).0.10$ $H_2O$: Calc. C, 55.51; H, 6.80; N, 6.50. Found C, 55.49; H, 6.82; N, 6.36.

HPLC: (Vydac C18 Column; gradient from 95/5 to 0/100 $H_2O/CH_3CN$ with 0.1% TFA. 15 min. gradient, flow rate=1.5 ml/min.) $R_t$=10.4 min. Purity=100%

$^1$HNMR: Consistent with structure.

FABMS: m/z=594 (M+ +H).

EXAMPLE 31

To a solution of endo-(1S)-1'-(((2-amino-7,7-dimethylbicyclo(2.2.1)-hept-1-yl)-methyl)-sulfonyl)-spiro(1H-indan-1,4'-piperidine (270 mg; 0.689 mmol) in methylene chloride (30 mL) was added 1-hydroxybenzotriazole (136 mg; 1.03 mmol), 1-(3-dimethylaminopropyl)-3-ethylcarbodiimide (193 mg; 1.03 mmol), and N-benzyloxycarbonyl-4-oxo-L-proline (270 mg; 1.0 mmol). After 18 hr the solution was concentrated, then partitioned between ethyl acetate (300 mL) and 1M HCl (300 mL). The organic layer was washed with 1M NaOH (2×300 mL), dried over sodium sulfate then concentrated. Purification by flash chromatography (5% methanol in methylene chloride) afforded the title compound (427 mg; 95%).

Anal: $(C_{36}H_{45}N_3O_6S).0.15$ $H_2O.0.15$ $CH_2Cl_2$ Calc. C, 65.46; H, 6.93; N, 6.34. Found C, 65.47; H, 6.84; N, 6.09.

HPLC: (Vydac C18 Column; gradient from 95/5 to 0/100 $H_2O/CH_3CN$ with 0.1% TFA. 15 min. gradient, flow rate=1.5 ml/min.) $R_t$=14.51 min. Purity=100%.

$^1$HNMR: Consistent with structure.

FABMS: m/z=648 (M+ +H).

EXAMPLE 32

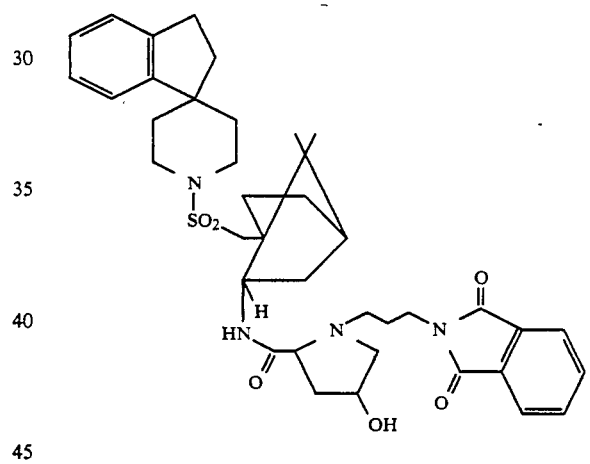

To a stirred solution of endo-(1S)-1'(((2-amino-7,7-dimethylbicyclo(2.2.1)-hept-1-yl)-methyl)sulfonyl)-spiro(1H-indan-1,4'-piperidine (94 mg; 0.17 mmol) in ethanol (20 mL) was added N-(3-bromopropyl)-phthalimide (69 mg; 0.255 mmol) followed by diisopropylethyl amine (0.044 mL; 0.255 mmol). The temperature was then increased to 50° C. After approximately 18 hr the solution was cooled then concentrated under reduced pressure. The residue was dissolved in methylene chloride (150 mL), washed with 1M HCl (2×150 mL) then dried over sodium sulfate and concentrated. Purification by flash chromatography (5% methanol in methylene chloride) afforded the title compound (45 mg; 40%) as a white solid.

Anal: $(C_{39}H_{50}N_4O_6S).0.10$ $H_2O.0.15$ $CH_2Cl_2$: Calc. C, 65.54; H, 7.10; N, 7.81. Found C, 65.52; H, 7.09; N, 7.71.

HPLC: (Vydac C18 Column; gradient from 95/5 to 0/100 $H_2O/CH_3CN$ with 0.1% TFA. 15 min. gradient, flow rate=1.5 ml/min.) $R_t$=13.81 min. Purity=100%.

$^1$HNMR: Consistent with structure

FABMS: m/z=703 (M+ +H)

TABLE

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

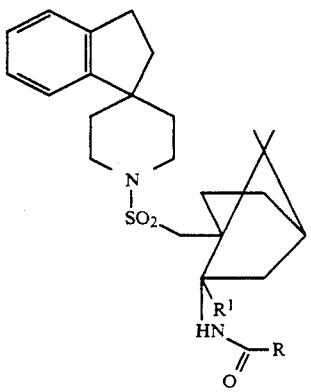

$R^1$ is hydrogen or hydroxy

R = 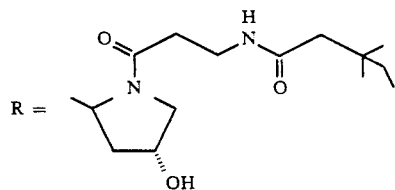

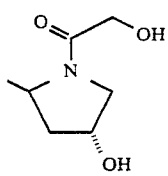

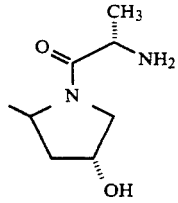

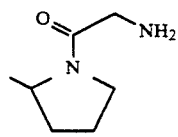

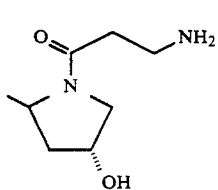

-continued

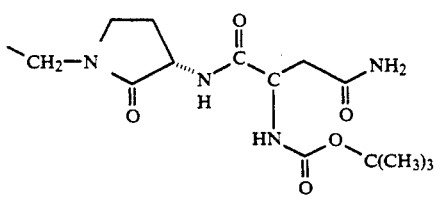

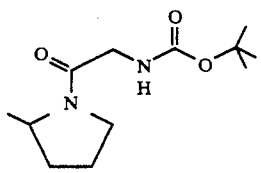

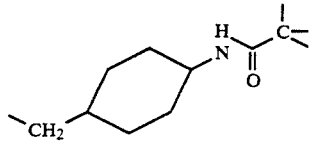

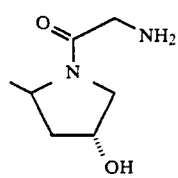

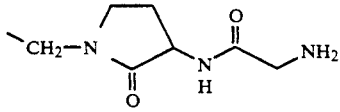

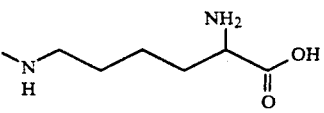

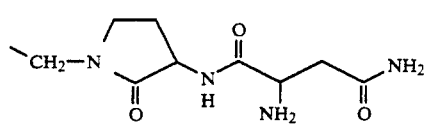

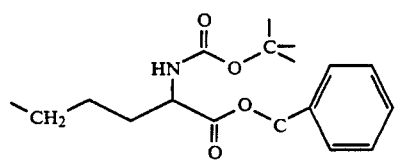

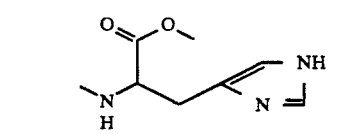

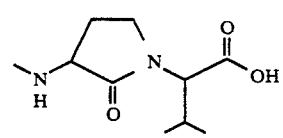

-continued

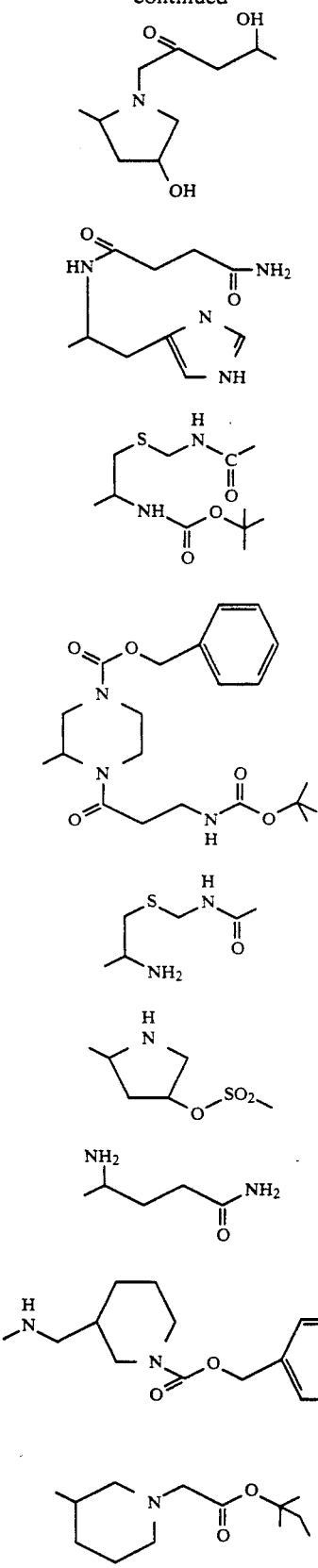
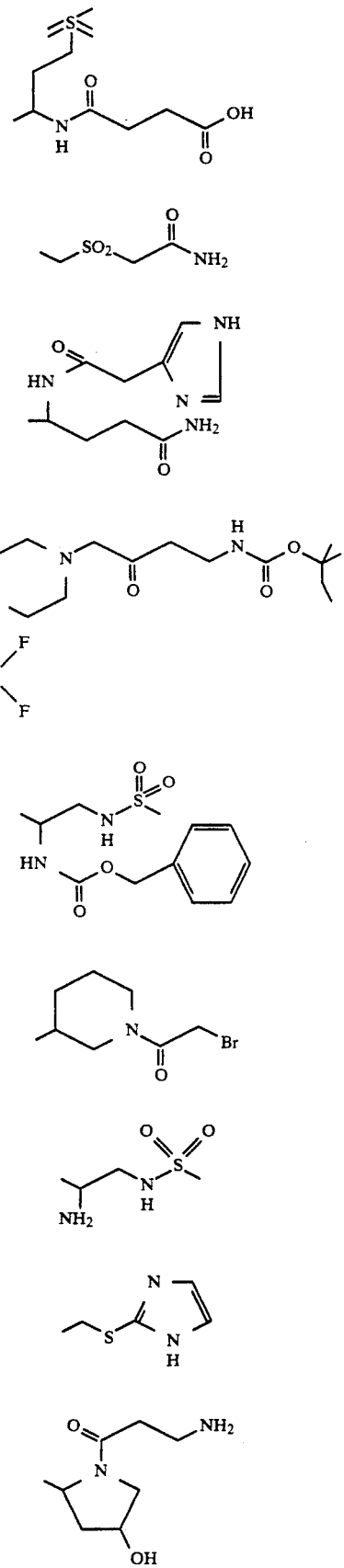

55
-continued
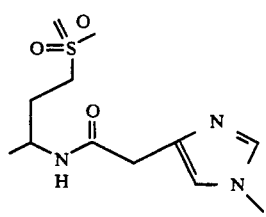
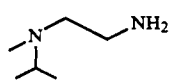
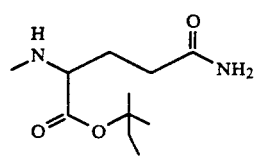
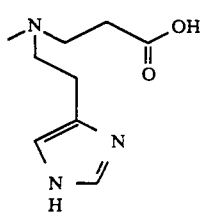
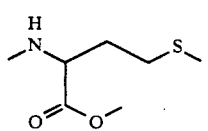
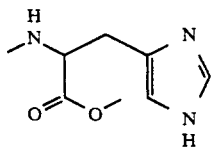
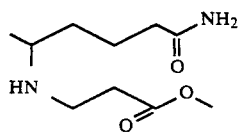
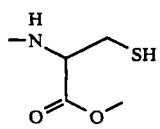
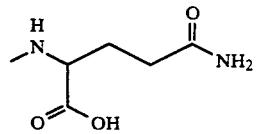
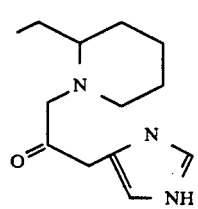
56
-continued
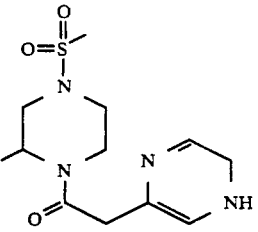
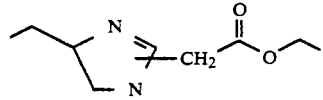
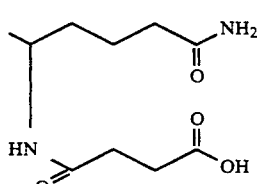
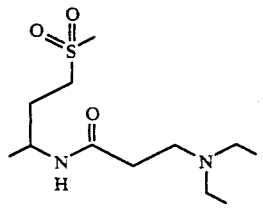
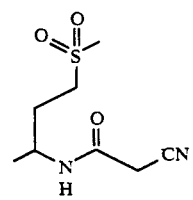
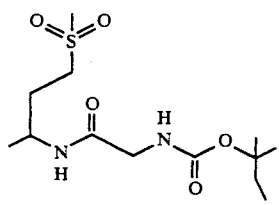
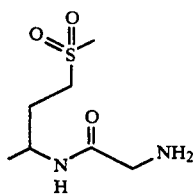
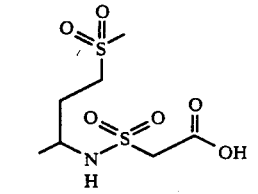

-continued
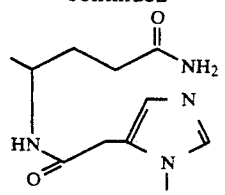
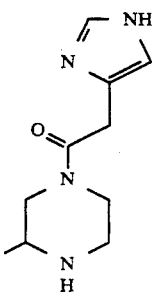
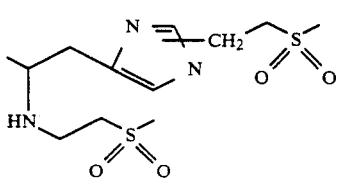
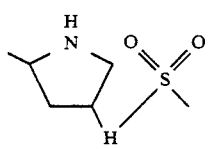
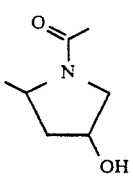
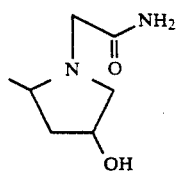
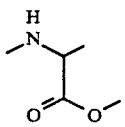
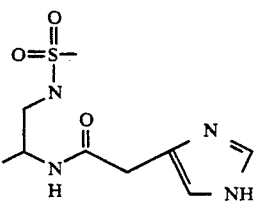
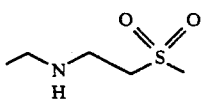
-continued
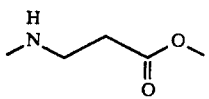
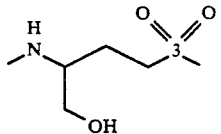
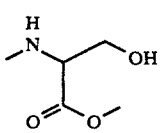
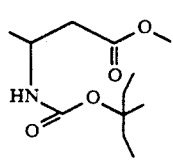
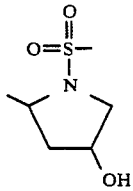
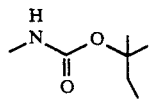
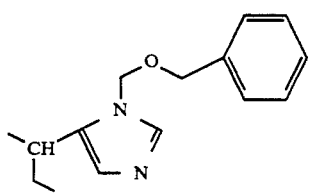
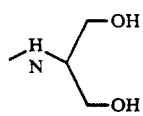
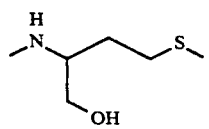
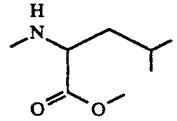
RADIOGLAND BINDING ASSAYS
The high affinity binding of [$^3$H] Oxytocin (OT) ([tyrosyl, 3,5-[$^3$H]OT; 30–60 Ci/mmol; New England Nuclear, Boston, MA) to uterine OT receptors was based on an assay* using a crude membrane preparation of uteri taken from diethylstilbestrol dipropionate (DES)-treated (0.3 mg/kg, ip; 18–24) rats. Competition studies were conducted at equilibrium (60 minutes; 22° C.) sing 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 μM unlabeled OT and the binding reaction was terminated by filtration through glass fiber filters using a cell harvester (model 7019, Skatron, Inc., Sterling, VA). IC$_{50}$ (the concentration of tested compound that inhibits 0% of OT) was reported, unless otherwise noted.

* Fuchs, A-R; Fuchs, F; Soloff, MS. 1985 J. Clin. Endocrinol. Metab. 60:37.

The measurement of [$^3$H]Vasopressin (AVP) ([phenylalanyl-3,4,5-$^3$H]AVP; 80–90 Ci/mmol; New England Nuclear)binding to a crude membrane preparation of male rat liver (AVP-V$_1$ sites) or kidney medulla (AVP-V$_2$ sites) was determined according to the method of Butlen, et al.** Competition assays were conducted at equilibrium (30 minutes at 30° C.) using 1 nM [$^3$H]AVP (liver) or 2 nM [$^3$H]AVP (kidney) in the following assay buffer: 100 mM Tris-HCl, 5 mM MgCl$_2$, 0.1% BSA, 50 μM phenylmethylsulfonylfluoride, and 50 μg/ml bactracin, pH 8.0. Nonspecific binding (5–10% of the total binding) was determined using 10 μM unlabeled AVP, and the binding reaction was terminated by filtration as described above for the [$^3$H]OT binding assay.

** Butlen, D; Guillon, G; Rajerison, R. M.; Jard, S; Sawyer, W. H.; Manning, M. 1978 Mol Pharmacol 14:1006.

K$_i$ values were obtained for each compound from three to six separate determinations of the IC$_{50}$ values (K$_i$=IC$_{50}$/1+c/K$_d$)*** using K$_d$ values obtained from saturation binding assay: [$^3$]OT (uterus), 0.7 nM; [$^3$H]AVP (liver), 0.4 nM; [$^3$H] (kidney), 1.4 nM.

*** Cheng, Y-C; Prusoff, W. H.; 1973 Biochem Pharmacol 22:3099

While the invention has been described and illustrated with reference to certain preferred embodimens thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula:

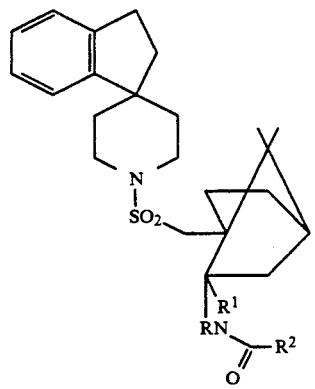

and the pharmaceutically acceptable salts thereof, wherein

R is H or C$_{2-5}$ alkylsulfonylalkyl,

R$^1$ is hydrogen,

R$^2$ is one of N-(R$^3$)$_2$, Het-R$^4$ or Alk-R$^5$, wherein

R$^3$ is independently one or more of hydrogen, cycloalkyl, pyrrolidinyl substituted by oxo, carboxyalkyl or alkoxycarbonylalkyl, alkyl substituted by alkylamino, alkylcarbamate, alkylcarbonyl, alkylsulfonyl, alkylthio, alkoxycarbonyl, amino, aminocarbonyl, carboxyl, dialkylamino, dialkylaminoaryl, hydroxyl, sulfhydryl, or substituted or unsubstituted 5 or 6 membered heterocyclic rings having 1 or 2 heteroatoms where said heteroatom is N and said ring substituent is aralkoxycarbonyl;

Het is a 5 or 6 membered heterocyclic ring having 1 or 2 heteroatom wherein said heteroatom is N, R$^4$ is alkylsulfonyl, alkylsulfonylamino, alkylsulfonyloxy, alkylaminocarbonyl, alkylcarbamatealkylcarbonyl, alkoxycarbonyl, alkoxycarbonylalkyl, aminocarbonylalkyl, aminoalkylcarbonyl, aralkoxycarbonyl, carbonyl, dialkylaminocarbonyl, dialkylaminoalkylcarbonyl, diaminoalkylcarbonyl, halogenalkyl, halogenalkylcarbonyl, halogenalkoxycarbonyl, hydroxy, hydroxyalkyl, hydroxyalkylcarbonyl, imidazolylalkylcarbonyl imidizinylalkylcarbonyl, or phthalimidinylalkyl; with the proviso for Het-R4 that Het cannot be mono-substituted by any one of the alkoxycarbonyl, alkoxycarbonylalkyl, aralkoxycarbonyl or hydroxy;

Alk is alkyl,

R$^5$ is independently one or more of R$^6$, or Het-R$^7$ wherein R$^6$ is independently one or more of alkylcarbamate, alkylcarbonylamino substituted by substituted imidazolyl or pyrrolidinyl rings where said ring substituent is alkyl or alkoxycarbonylalky, alkylcarbamatecycloalkyl, alkylcarbonylaminoalkylsulfonyl, alkylimidazolylthio, alkylimidizinylthio, alkylimidazolylalkylthio, alkylimidizinylalkylthio, alkylpyrrolidinylthio, alkylpyrrolidinylalkylthio, alkylsulfonyl, alkylsulfonylamino, alkylsulfonylalkylamino, alkoxycarbonyl, alkoxycarbonylalkylamine, alkoxycarbonylalkylcarbonylamine, alkoxycarbonylalkylsulfonylamine, amino, aminocarbonyl, aminoalkylcarbonylamino, aminocarbonylalkylsulfonyl, aminocarbonylalkylecarbonylamino, aralkoxy, aralkoxycarbonyl, aralkylcarbamate, arylcarbamate, arylcarbamatecarbonylamino, arylcarbamatealkylcarbonylamino, carboxyalkylamino, carboxyalkylcarbonylamino, carboxyalkylsulfonylamino, cyano, cyanoalkylcarbonylamino, dialkylaminoalkylcarbonylamino or oxo, with the proviso for $R^6$ that $R^6$ cannot be mono-substituted by any one of alkoxycarbonyl, alkylcarbamate, alkylsulfonyl, aralkylcarbamate, aralkoxy, amino, aminocarbonyl, or oxo;

Het is as defined before;

$R^7$ is one or more of alkyl, imidazolinylalkylcarbonyl, imidazolinylalkylcarbonylamino, oxo, pyrrolidinylalkylcarbonyl, pyrrolidinylalkylcarbonylamino or alkylamino substituted by one or more of alkylcarbamate, alkylcarbamatealkylcarbonyl, alkylsulfonylalkyl, amino, aralkoxyalkyl or oxo with the proviso for Het-$R^7$ that Het cannot be mono-substituted by alkyl alkylamino, dialkylamino or oxo.

2. A compound of the formula:

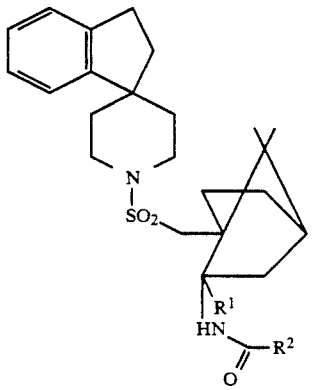

and the pharmaceutically acceptable salts thereof, wherein $R^1$ is hydrogen, $R^2$ is one of NH-$R^3$, Het-$R^4$ or Alk-$R^5$, wherein $R^3$ is cycloalkyl, pyrrolidinyl substituted by oxo, carboxyalkyl or alkoxycarbonylalkyl, alkyl substituted by alkylcarbamate, alkylcarbonyl, alkylsulfonyl, alkylthio, alkoxycarbonyl, amino, aminocarbonyl, carboxyl, hydroxyl, sulfhydryl, or substituted or unsubstituted 5 or 6 membered heterocyclic rings having 1 or 2 heteroatoms where said heteroatom is N and said ring substitutent is aralkoxycarbonyl;

Het is a 5 or 6 membered heterocyclic ring having 1 heteroatom wherein said heteroatom is N, $R^4$ is alkylsulfonyl, alkylsulfonyloxy, alkylaminocarbonyl, alkylcarbamatealkylcarbonyl, alkoxycarbonyl, alkoxycarbonylalkyl, aminocarbonylalkyl, aminoalkylcarbonyl, aralkoxycarbonyl, carbonyl, dialkylaminocarbonyl, diaminoalkylcarbonyl, halogenalkyl, halogenalkoxycarbonyl, hydroxy, hydroxyalkyl, hydroxyalkylcarbonyl, imidazolylalkylcarbonyl or phthalimidinylalkyl; with the proviso for Het-R4 that Het cannot be mono-substituted by any one of the alkoxycarbonyl, alkoxycarbonylalkyl, aralkoxycarbonyl or hydroxy;

Alk is alkyl, $R^5$ is independently one or more of $R^6$, or Het-$R^7$ wherein $R^6$ is independently one or more of alkylcarbamate, alkylcarbonylamino substituted by substituted imidazolyl or pyrrolidinyl rings where said ring substituent is alkyl or alkoxycarbonylalky, alkylcarbamatecycloalkyl, alkylcarbonylaminoalkylsulfonyl, alkylimidazolylthio, alkylimidazolylalkylthio, alkylpyrrolidinylthio, alkylpyrrolidinylalkylthio, alkylsulfonyl, alkylsulfonylamino, alkylsulfonylalkylamino, alkoxycarbonyl, alkoxycarbonylalkylamine, alkoxycarbonylalkylcarbonylamine, alkoxycarbonylalkylsulfonylamine, amino, aminocarbonyl, aminoalkylcarbonylamino, aminocarbonylalkylsulfonyl, aminocarbonylalkylearbonylamino, aralkoxy, aralkoxycarbonyl, aralkylcarbamate, arylcarbamate, arylcarbamatecarbonylamino, arylcarbamatealkylcarbonylamino, carboxyalkylamino, carboxyalkylcarbonylamino, carboxyalkylsulfonylamino, cyano, cyanoalkylcarbonylamino, dialkylaminoalkylcarbonylamino or oxo, with the proviso for $R^6$ that $R^6$ cannot be mono-substituted by any one of alkoxycarbonyl, alkylcarbamate, alkylsulfonyl, aralkylcarbamate, aralkoxy, amino, aminocarbonyl, or oxo;

Het is as defined before;

$R^7$ is one or more of alkyl, imidazolinylalkylcarbonyl, imidazolinylalkylcarbonylamino, oxo, pyrrolidinylalkylcarbonyl, pyrrolidinylalkylcarbonylamino or alkylamino substituted by one or more of alkylcarbamate, alkylcarbamatealkylcarbonyl, alkysulfonylalkyl, amino, aralkoxyalkyl or oxo with the proviso for Het-$R^7$ that Het cannot be mono-substituted by alkyl alkylamino, dialkylamino or oxo.

3. A pharmaceutical composition comprising a pharmaceutically acceptable carrier and a compound as claimed in claim 1 in a quantity sufficient to antagonize binding of oxytocin to its receptor site.

4. A pharmaceutical composition comprising a pharmaceutically acceptable carrier and a compound as claimed in claim 1 in a quantity sufficient to prevent preterm labor in a mammal.

5. A pharmaceutical composition comprising a pharmaceutically acceptable carrier and a compound as claimed in claim 1 in an amount sufficient to stop labor prior to cesarian delivery in a mammal.

6. A pharmaceutical composition comprising a pharmaceutically acceptable carrier and a compound as claimed in claim 1, in an amount sufficient to treat dysmenorrhea.

* * * * *